(12) United States Patent
Henry

(10) Patent No.: US 8,960,196 B2
(45) Date of Patent: *Feb. 24, 2015

(54) MASK SYSTEM WITH INTERCHANGEABLE HEADGEAR CONNECTORS

(71) Applicant: ResMed Limited, Bella Vista, NSW (AU)

(72) Inventor: Robert Edward Henry, Bella Vista (AU)

(73) Assignee: ResMed Limited, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/904,748

(22) Filed: May 29, 2013

(65) Prior Publication Data

US 2013/0255673 A1     Oct. 3, 2013

Related U.S. Application Data

(63) Continuation of application No. 12/010,680, filed on Jan. 29, 2008, now Pat. No. 8,517,023.

(60) Provisional application No. 60/898,108, filed on Jan. 30, 2007.

(51) Int. Cl.
| | |
|---|---|
| *A61M 11/00* | (2006.01) |
| *A61M 16/06* | (2006.01) |
| *A61M 16/08* | (2006.01) |
| *A62B 18/08* | (2006.01) |

(52) U.S. Cl.
CPC ........... *A61M 16/0683* (2013.01); *A61M 16/06* (2013.01); *A61M 16/0816* (2013.01); *A62B 18/084* (2013.01); *A61M 16/0638* (2013.01)

USPC ........... 128/207.11; 128/206.26; 128/205.25; 128/206.12; 128/206.21; 128/206.28

(58) Field of Classification Search
USPC ............. 128/202.27, 205.25, 206.11–206.18, 128/206.21, 206.23–206.28, 207.11, 207.13
See application file for complete search history.

(56) References Cited

U.S. PATENT DOCUMENTS

| | | |
|---|---|---|
| 364,934 A | 6/1887 | Bright |
| 428,592 A | 5/1890 | Chapman |
| 443,191 A | 12/1890 | Illing |
| 781,516 A | 1/1905 | Guthrie |

(Continued)

FOREIGN PATENT DOCUMENTS

| | | |
|---|---|---|
| AU | 91/77110 | 11/1991 |
| AU | 94/64816 | 12/1994 |

(Continued)

OTHER PUBLICATIONS 9 photographs of Weinmann mask, WM 23122, 1991.

(Continued)

*Primary Examiner* — Steven Douglas
(74) *Attorney, Agent, or Firm* — Nixon & Vanderhye, P.C.

(57) ABSTRACT

A mask system for delivering breathable gas to a patient includes a common frame provided without built-in or integral headgear attachment points and at least first and second headgear connectors adapted to be provided to the frame. Each of the at least first and second headgear connectors are adapted to attach headgear straps of headgear. The at least first and second headgear connectors are different from one another in at least one aspect.

86 Claims, 16 Drawing Sheets

(56) References Cited

U.S. PATENT DOCUMENTS

| | | |
|---|---|---|
| 812,706 A | 2/1906 | Warbasse |
| 1,081,745 A | 12/1913 | Johnston et al. |
| 1,125,542 A | 1/1915 | Humphries |
| 1,176,886 A | 3/1916 | Ermold |
| 1,192,186 A | 7/1916 | Greene |
| 1,206,045 A | 11/1916 | Smith |
| 1,229,050 A | 6/1917 | Donald |
| 1,282,527 A | 10/1918 | Bidonde |
| 1,362,766 A | 12/1920 | McGargill |
| 1,445,010 A | 2/1923 | Feinberg |
| 1,502,450 A | 7/1924 | Wood |
| 1,610,793 A | 12/1926 | Kaufman |
| 1,632,449 A | 6/1927 | McKesson |
| 1,653,572 A | 12/1927 | Jackson |
| 1,710,160 A | 4/1929 | Gibbs |
| 1,837,591 A | 12/1931 | Shindel |
| 1,873,160 A | 8/1932 | Sturtevant |
| 1,926,027 A | 9/1933 | Biggs |
| 2,011,733 A | 8/1935 | Shindel |
| 2,104,016 A | 1/1938 | Biggs |
| 2,123,353 A | 7/1938 | Catt |
| 2,127,136 A | 8/1938 | Pobirs |
| 2,130,555 A | 9/1938 | Malcom |
| 2,133,699 A | 10/1938 | Heidbrink |
| 2,149,067 A | 2/1939 | Otero |
| 2,166,164 A | 7/1939 | Lehmberg |
| 2,245,658 A | 6/1941 | Erickson |
| 2,245,969 A | 6/1941 | Francisco et al. |
| 2,248,477 A | 7/1941 | Lombard |
| 2,254,854 A | 9/1941 | O'Connell |
| 2,317,608 A | 4/1943 | Heidbrink |
| 2,353,643 A | 7/1944 | Bulbulian |
| 2,444,417 A | 2/1945 | Bierman |
| 2,371,965 A | 3/1945 | Lehmberg |
| 2,376,871 A | 5/1945 | Fink |
| 2,382,364 A | 8/1945 | Yant |
| 2,415,846 A | 2/1947 | Randall |
| 2,428,451 A | 10/1947 | Emerson |
| 2,433,565 A | 12/1947 | Korman |
| 2,438,058 A | 3/1948 | Kincheloe |
| 2,473,518 A | 6/1949 | Garrard et al. |
| D156,060 S | 11/1949 | Wade |
| D161,337 S | 12/1950 | Hill |
| 2,540,567 A | 2/1951 | Bennett |
| 2,578,621 A | 12/1951 | Yant |
| 2,590,006 A | 3/1952 | Gordon |
| 2,625,155 A | 1/1953 | Engelder |
| 2,641,253 A | 6/1953 | Engelder |
| 2,693,178 A | 11/1954 | Gilroy |
| 2,706,983 A | 4/1955 | Matheson et al. |
| 2,749,910 A | 6/1956 | Faulconer, Jr. |
| RE24,193 E | 8/1956 | Emerson |
| 2,820,651 A | 1/1958 | Phillips |
| 2,837,090 A | 6/1958 | Bloom et al. |
| 2,868,196 A | 1/1959 | Stampe |
| 2,875,757 A | 3/1959 | Galleher, Jr. |
| 2,875,759 A | 3/1959 | Galleher, Jr. |
| 2,881,444 A | 4/1959 | Fresh et al. |
| 2,882,895 A | 4/1959 | Galeazzi |
| 2,902,033 A | 9/1959 | Galleher, Jr. |
| 2,917,045 A | 12/1959 | Schildknecht et al. |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher, Jr. |
| 3,042,035 A | 7/1962 | Coanda |
| 3,117,574 A | 1/1964 | Replogle |
| 3,182,659 A | 5/1965 | Blount |
| 3,189,027 A | 6/1965 | Bartlett, Jr. |
| 3,193,624 A | 7/1965 | Webb et al. |
| 3,238,943 A | 3/1966 | Holley |
| 3,288,138 A | 11/1966 | Sachs |
| 3,315,672 A | 4/1967 | Cunningham et al. |
| 3,315,674 A | 4/1967 | Bloom et al. |
| 3,330,273 A | 7/1967 | Bennett |
| 3,330,274 A | 7/1967 | Bennett |
| 3,362,420 A | 1/1968 | Blackburn et al. |
| 3,363,833 A | 1/1968 | Laerdal |
| 3,545,436 A | 12/1970 | Holloway |
| 3,556,122 A | 1/1971 | Laerdal |
| 3,580,051 A | 5/1971 | Blevins |
| 3,670,726 A | 6/1972 | Mahon et al. |
| 3,682,171 A | 8/1972 | Dali et al. |
| 3,700,000 A | 10/1972 | Hesse et al. |
| 3,720,235 A | 3/1973 | Schrock |
| 3,725,953 A | 4/1973 | Johnson et al. |
| 3,739,774 A | 6/1973 | Gregory |
| 3,750,333 A | 8/1973 | Vance |
| 3,752,157 A | 8/1973 | Malmin |
| 3,754,552 A | 8/1973 | King |
| 3,796,216 A | 3/1974 | Schwarz |
| 3,799,164 A | 3/1974 | Rollins |
| D231,803 S | 6/1974 | Huddy |
| 3,830,230 A | 8/1974 | Chester |
| 3,861,385 A | 1/1975 | Carden |
| 3,902,486 A | 9/1975 | Guichard |
| 3,905,361 A | 9/1975 | Hewson et al. |
| 3,910,261 A | 10/1975 | Ragsdale et al. |
| 3,938,614 A | 2/1976 | Ahs |
| 3,972,321 A | 8/1976 | Proctor |
| 3,978,854 A | 9/1976 | Mills, Jr. |
| 4,006,744 A | 2/1977 | Steer |
| 4,062,357 A | 12/1977 | Laerdal |
| 4,069,516 A | 1/1978 | Watkins, Jr. |
| 4,077,404 A | 3/1978 | Elam |
| D248,497 S | 7/1978 | Slosek |
| D250,131 S | 10/1978 | Lewis et al. |
| 4,120,302 A | 10/1978 | Ziegler |
| 4,142,527 A | 3/1979 | Garcia |
| 4,153,051 A | 5/1979 | Shippert |
| 4,156,426 A | 5/1979 | Gold |
| 4,167,185 A | 9/1979 | Lewis |
| 4,201,205 A | 5/1980 | Bartholomew |
| 4,226,234 A | 10/1980 | Gunderson |
| 4,231,363 A | 11/1980 | Grimes |
| 4,233,972 A | 11/1980 | Hauff et al. |
| 4,239,038 A | 12/1980 | Holmes |
| 4,245,632 A | 1/1981 | Houston |
| 4,248,218 A | 2/1981 | Fischer |
| 4,263,908 A | 4/1981 | Mizerak |
| 4,264,743 A | 4/1981 | Maruyama et al. |
| 4,265,239 A | 5/1981 | Fischer, Jr. et al. |
| 4,266,540 A | 5/1981 | Panzik et al. |
| 4,267,845 A | 5/1981 | Robertson, Jr. et al. |
| 4,273,124 A | 6/1981 | Zimmerman |
| D262,322 S | 12/1981 | Mizerak |
| 4,304,229 A | 12/1981 | Curtin |
| 4,312,359 A | 1/1982 | Olson |
| 4,328,797 A | 5/1982 | Rollins et al. |
| 4,337,767 A | 7/1982 | Yahata |
| 4,347,205 A | 8/1982 | Stewart |
| 4,354,488 A | 10/1982 | Bartos |
| 4,367,735 A | 1/1983 | Dali |
| 4,367,816 A | 1/1983 | Wilkes |
| 4,369,284 A | 1/1983 | Chen |
| 4,402,316 A | 9/1983 | Gadberry |
| 4,406,283 A | 9/1983 | Bir |
| 4,412,537 A | 11/1983 | Tiger |
| 4,414,973 A | 11/1983 | Matheson et al. |
| 4,417,575 A | 11/1983 | Hilton et al. |
| 4,422,456 A | 12/1983 | Tiep |
| 4,446,576 A | 5/1984 | Hisataka |
| 4,449,526 A | 5/1984 | Elam |
| 4,454,880 A | 6/1984 | Muto et al. |
| 4,454,881 A | 6/1984 | Huber et al. |
| 4,455,675 A | 6/1984 | Bose et al. |
| 4,458,679 A | 7/1984 | Ward |
| 4,467,799 A | 8/1984 | Steinberg |
| 4,493,614 A | 1/1985 | Chu et al. |
| 4,522,639 A | 6/1985 | Ansite et al. |
| 4,548,200 A | 10/1985 | Wapner |
| 4,549,542 A | 10/1985 | Chien |
| 4,558,710 A | 12/1985 | Eichler |
| 4,572,323 A | 2/1986 | Randall |

(56) References Cited

U.S. PATENT DOCUMENTS

| | | |
|---|---|---|
| 4,579,113 A | 4/1986 | McCreadie et al. |
| 4,587,967 A | 5/1986 | Chu et al. |
| 4,593,688 A | 6/1986 | Payton |
| 4,601,465 A | 7/1986 | Roy |
| D285,496 S | 9/1986 | Berman |
| 4,616,647 A | 10/1986 | McCreadie |
| 4,617,637 A | 10/1986 | Chu et al. |
| 4,622,964 A | 11/1986 | Flynn |
| 4,630,604 A | 12/1986 | Montesi |
| 4,641,645 A | 2/1987 | Tayebi |
| 4,641,647 A | 2/1987 | Behan |
| D289,238 S | 4/1987 | Arthur, Jr. |
| 4,655,213 A | 4/1987 | Rapoport et al. |
| 4,657,010 A | 4/1987 | Wright |
| 4,660,555 A | 4/1987 | Payton |
| 4,665,570 A | 5/1987 | Davis |
| 4,671,267 A | 6/1987 | Stout |
| 4,671,271 A | 6/1987 | Bishop et al. |
| 4,674,134 A | 6/1987 | Lundin |
| 4,676,241 A | 6/1987 | Webb et al. |
| 4,677,975 A | 7/1987 | Edgar et al. |
| 4,677,977 A | 7/1987 | Wilcox |
| 4,686,977 A | 8/1987 | Cosma |
| 4,699,139 A | 10/1987 | Marshall et al. |
| 4,706,664 A | 11/1987 | Snook et al. |
| 4,707,863 A | 11/1987 | McNeal |
| 4,711,636 A | 12/1987 | Bierman |
| 4,713,844 A | 12/1987 | Westgate |
| H397 H | 1/1988 | Stark |
| D293,613 S | 1/1988 | Wingler |
| 4,739,755 A | 4/1988 | White et al. |
| 4,753,233 A | 6/1988 | Grimes |
| 4,767,411 A | 8/1988 | Edmunds |
| 4,770,169 A | 9/1988 | Schmoegner et al. |
| 4,772,760 A | 9/1988 | Graham |
| 4,774,941 A | 10/1988 | Cook |
| 4,774,946 A | 10/1988 | Ackerman et al. |
| 4,782,832 A | 11/1988 | Trimble et al. |
| 4,790,829 A | 12/1988 | Bowden et al. |
| 4,799,477 A | 1/1989 | Lewis |
| 4,802,857 A | 2/1989 | Laughlin |
| 4,803,981 A | 2/1989 | Vickery |
| 4,807,617 A | 2/1989 | Nesti |
| 4,809,692 A | 3/1989 | Nowacki et al. |
| 4,811,730 A | 3/1989 | Milano |
| 4,819,629 A | 4/1989 | Jonson |
| 4,821,713 A | 4/1989 | Bauman |
| 4,827,924 A | 5/1989 | Japuntich |
| 4,830,138 A | 5/1989 | Palmaer et al. |
| 4,832,017 A | 5/1989 | Schnoor |
| 4,838,878 A | 6/1989 | Kalt et al. |
| 4,841,953 A | 6/1989 | Dodrill |
| 4,848,334 A | 7/1989 | Bellm |
| 4,848,366 A | 7/1989 | Aita et al. |
| 4,850,346 A | 7/1989 | Michel et al. |
| 4,856,118 A | 8/1989 | Sapiejewski |
| D304,384 S | 10/1989 | Derobert |
| 4,886,058 A | 12/1989 | Brostrom et al. |
| 4,899,740 A | 2/1990 | Napolitano |
| 4,905,683 A | 3/1990 | Cronjaeger |
| 4,907,584 A | 3/1990 | McGinnis |
| 4,910,806 A | 3/1990 | Baker et al. |
| 4,914,957 A | 4/1990 | Dougherty |
| 4,915,105 A | 4/1990 | Lee |
| 4,915,106 A | 4/1990 | Aulgur et al. |
| 4,919,128 A | 4/1990 | Kopala et al. |
| 4,919,654 A | 4/1990 | Kalt |
| 4,938,210 A | 7/1990 | Shene |
| 4,938,212 A | 7/1990 | Snook et al. |
| 4,941,476 A | 7/1990 | Fisher |
| 4,944,310 A | 7/1990 | Sullivan |
| 4,945,907 A | 8/1990 | Tayebi |
| 4,947,860 A | 8/1990 | Fisher |
| D310,431 S | 9/1990 | Bellm |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| D313,277 S | 12/1990 | Haining |
| 4,976,698 A | 12/1990 | Stokley |
| 4,986,269 A | 1/1991 | Hakkinen |
| 4,989,271 A | 2/1991 | Sapiejewski et al. |
| 4,989,596 A | 2/1991 | Macris et al. |
| 4,989,599 A | 2/1991 | Carter |
| 4,996,983 A | 3/1991 | Amrhein |
| 5,000,173 A | 3/1991 | Zalkin et al. |
| 5,003,631 A | 4/1991 | Richardson |
| 5,003,633 A | 4/1991 | Itoh |
| 5,005,568 A | 4/1991 | Loescher et al. |
| 5,005,571 A | 4/1991 | Dietz |
| 5,018,519 A | 5/1991 | Brown |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,027,809 A | 7/1991 | Robinson |
| 5,038,772 A | 8/1991 | Kolbe et al. |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,046,491 A | 9/1991 | Derrick |
| 5,062,421 A | 11/1991 | Burns et al. |
| 5,063,922 A | 11/1991 | Hakkinen |
| 5,069,205 A | 12/1991 | Urso |
| 5,074,297 A | 12/1991 | Venegas |
| 5,080,092 A | 1/1992 | Tenna |
| D323,908 S | 2/1992 | Hollister et al. |
| 5,093,940 A | 3/1992 | Nishiyama |
| 5,109,839 A | 5/1992 | Blasdell et al. |
| 5,109,840 A | 5/1992 | Daleiden |
| 5,113,857 A | 5/1992 | Dickerman et al. |
| 5,117,818 A | 6/1992 | Palfy |
| 5,121,745 A | 6/1992 | Israel |
| 5,121,746 A | 6/1992 | Sikora |
| 5,123,677 A | 6/1992 | Kreczko et al. |
| 5,127,397 A | 7/1992 | Kohnke |
| 5,133,347 A | 7/1992 | Huennebeck |
| 5,137,017 A | 8/1992 | Salter |
| 5,138,722 A | 8/1992 | Urella et al. |
| 5,140,980 A | 8/1992 | Haughey et al. |
| 5,140,982 A | 8/1992 | Bauman |
| 5,146,914 A | 9/1992 | Sturrock |
| 5,159,938 A | 11/1992 | Laughlin |
| 5,178,138 A | 1/1993 | Walstrom et al. |
| 5,181,506 A | 1/1993 | Tardiff, Jr. et al. |
| D333,015 S | 2/1993 | Farmer et al. |
| 5,188,101 A | 2/1993 | Tumolo |
| D334,633 S | 4/1993 | Rudolph |
| 5,199,424 A | 4/1993 | Sullivan et al. |
| D335,322 S | 5/1993 | Jones |
| 5,207,665 A | 5/1993 | Davis et al. |
| 5,220,699 A | 6/1993 | Farris |
| 5,222,478 A | 6/1993 | Scarberry et al. |
| 5,231,983 A | 8/1993 | Matson et al. |
| 5,233,978 A | 8/1993 | Callaway |
| 5,243,709 A | 9/1993 | Sheehan et al. |
| 5,243,971 A | 9/1993 | Sullivan et al. |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,279,289 A | 1/1994 | Kirk |
| 5,280,784 A | 1/1994 | Kohler |
| 5,291,880 A | 3/1994 | Almovist et al. |
| 5,299,448 A | 4/1994 | Maryyanek |
| 5,299,579 A | 4/1994 | Gedeon et al. |
| 5,299,599 A | 4/1994 | Farmer et al. |
| 5,301,689 A | 4/1994 | Wennerholm |
| 5,304,146 A | 4/1994 | Johnson et al. |

(56) References Cited

U.S. PATENT DOCUMENTS

| | | |
|---|---|---|
| 5,311,862 A | 5/1994 | Blasdell et al. |
| 5,322,057 A | 6/1994 | Raabe et al. |
| 5,322,059 A | 6/1994 | Walther |
| 5,331,691 A | 7/1994 | Runckel |
| D349,586 S | 8/1994 | Handke |
| 5,334,646 A | 8/1994 | Chen |
| 5,335,656 A | 8/1994 | Bowe et al. |
| 5,343,878 A | 9/1994 | Scarberry et al. |
| 5,349,949 A | 9/1994 | Schegerin |
| 5,353,789 A | 10/1994 | Schlobohm |
| 5,355,878 A | 10/1994 | Griffiths et al. |
| 5,355,893 A | 10/1994 | Mick et al. |
| 5,357,945 A | 10/1994 | Messina |
| 5,357,951 A | 10/1994 | Ratner |
| 5,364,367 A | 11/1994 | Banks et al. |
| 5,372,130 A | 12/1994 | Stern et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,388,571 A | 2/1995 | Roberts et al. |
| 5,390,373 A | 2/1995 | Flory |
| 5,391,248 A | 2/1995 | Brain |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,400,781 A | 3/1995 | Davenport |
| 5,404,871 A | 4/1995 | Goodman et al. |
| 5,411,021 A | 5/1995 | Gdulla et al. |
| 5,419,317 A | 5/1995 | Blasdell et al. |
| 5,419,318 A | 5/1995 | Tayebi |
| 5,425,359 A | 6/1995 | Liou |
| 5,429,126 A | 7/1995 | Bracken |
| 5,429,683 A | 7/1995 | Le Mitouard |
| 5,431,158 A | 7/1995 | Tirotta |
| 5,437,267 A | 8/1995 | Weinstein et al. |
| 5,438,981 A | 8/1995 | Starr et al. |
| 5,441,046 A | 8/1995 | Starr et al. |
| D362,061 S | 9/1995 | McGinnis et al. |
| 5,462,528 A | 10/1995 | Roewer |
| 5,477,852 A | 12/1995 | Landis et al. |
| 5,479,920 A | 1/1996 | Piper et al. |
| 5,481,763 A | 1/1996 | Brostrom et al. |
| 5,485,837 A | 1/1996 | Soles Bee et al. |
| 5,488,948 A | 2/1996 | Dubruille et al. |
| 5,492,116 A | 2/1996 | Scarberry et al. |
| 5,501,214 A | 3/1996 | Sabo |
| 5,503,147 A | 4/1996 | Bertheau |
| 5,509,404 A | 4/1996 | Lloyd et al. |
| 5,509,409 A | 4/1996 | Weatherholt |
| 5,511,541 A | 4/1996 | Dearstine |
| 5,513,634 A | 5/1996 | Jackson |
| 5,513,635 A | 5/1996 | Bedi |
| 5,517,986 A | 5/1996 | Starr et al. |
| 5,522,382 A | 6/1996 | Sullivan et al. |
| 5,526,806 A | 6/1996 | Sansoni |
| 5,533,506 A | 7/1996 | Wood |
| 5,538,000 A | 7/1996 | Rudolph |
| 5,538,001 A | 7/1996 | Bridges |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,568,946 A | 10/1996 | Jackowski |
| 5,570,682 A | 11/1996 | Johnson |
| 5,570,684 A | 11/1996 | Behr |
| 5,570,689 A | 11/1996 | Starr et al. |
| 5,575,278 A | 11/1996 | Bonhomme et al. |
| D377,089 S | 12/1996 | Starr et al. |
| 5,592,937 A | 1/1997 | Freund |
| 5,592,938 A | 1/1997 | Scarberry et al. |
| 5,608,647 A | 3/1997 | Rubsamen et al. |
| 5,617,849 A | 4/1997 | Springett et al. |
| 5,623,923 A | 4/1997 | Bertheau et al. |
| 5,642,726 A | 7/1997 | Owens et al. |
| 5,642,730 A | 7/1997 | Baran |
| 5,645,054 A | 7/1997 | Cotner et al. |
| 5,647,355 A | 7/1997 | Starr et al. |
| 5,647,356 A | 7/1997 | Osendorf et al. |
| 5,647,357 A | 7/1997 | Barnett et al. |
| 5,649,532 A | 7/1997 | Griffiths |
| 5,649,533 A | 7/1997 | Oren |
| 5,653,228 A | 8/1997 | Byrd |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,660,171 A | 8/1997 | Kimm et al. |
| 5,660,174 A | 8/1997 | Jacobelli |
| 5,662,101 A | 9/1997 | Ogden et al. |
| 5,666,946 A | 9/1997 | Langenback |
| 5,676,133 A | 10/1997 | Hickle et al. |
| D385,960 S | 11/1997 | Rudolph |
| 5,682,881 A | 11/1997 | Winthrop et al. |
| 5,685,296 A | 11/1997 | Zdrojkowski et al. |
| 5,687,715 A | 11/1997 | Landis et al. |
| D389,238 S | 1/1998 | Kirk, III et al. |
| 5,704,345 A | 1/1998 | Berthon-Jones |
| 5,707,342 A | 1/1998 | Tanaka |
| 5,709,204 A | 1/1998 | Lester |
| 5,715,814 A | 2/1998 | Ebers |
| 5,724,964 A | 3/1998 | Brunson et al. |
| 5,724,965 A | 3/1998 | Handke et al. |
| 5,735,272 A | 4/1998 | Dillon et al. |
| 5,740,795 A | 4/1998 | Brydon |
| 5,740,799 A | 4/1998 | Nielsen |
| 5,746,201 A | 5/1998 | Kidd |
| 5,752,509 A | 5/1998 | Lachmann et al. |
| 5,752,511 A | 5/1998 | Simmons et al. |
| 5,778,872 A | 7/1998 | Fukunaga et al. |
| 5,782,774 A | 7/1998 | Shmulewitz |
| 5,794,615 A | 8/1998 | Estes |
| 5,794,617 A | 8/1998 | Brunell et al. |
| 5,794,619 A | 8/1998 | Edeiman et al. |
| D398,987 S | 9/1998 | Cotner et al. |
| 5,807,341 A | 9/1998 | Heim |
| 5,813,423 A | 9/1998 | Kirchgeorg |
| 5,832,918 A | 11/1998 | Pantino |
| D402,755 S | 12/1998 | Kwok |
| 5,842,469 A | 12/1998 | Rapp et al. |
| RE36,165 E | 3/1999 | Behr |
| 5,884,624 A | 3/1999 | Barnett et al. |
| 5,887,587 A | 3/1999 | Groenke |
| 5,896,857 A | 4/1999 | Hely et al. |
| 5,906,203 A | 5/1999 | Klockseth et al. |
| 5,909,732 A | 6/1999 | Diesel et al. |
| 5,918,598 A | 7/1999 | Belfer et al. |
| 5,921,239 A | 7/1999 | McCall et al. |
| D412,745 S | 8/1999 | Scheu |
| 5,935,136 A | 8/1999 | Hulse et al. |
| 5,937,445 A | 8/1999 | Ravo et al. |
| 5,937,851 A | 8/1999 | Serowski et al. |
| 5,954,049 A | 9/1999 | Foley et al. |
| 5,964,485 A | 10/1999 | Hame et al. |
| 5,966,745 A | 10/1999 | Schwartz et al. |
| 5,970,975 A | 10/1999 | Estes et al. |
| 5,975,079 A | 11/1999 | Hellings et al. |
| 6,003,511 A | 12/1999 | Fukunaga et al. |
| 6,006,748 A | 12/1999 | Hollis |
| D419,658 S | 1/2000 | Matchett et al. |
| 6,016,804 A | 1/2000 | Gleason et al. |
| D421,298 S | 2/2000 | Kenyon et al. |
| 6,019,101 A | 2/2000 | Cotner et al. |
| 6,026,811 A | 2/2000 | Settle |
| 6,029,660 A | 2/2000 | Calluaud et al. |
| 6,029,665 A | 2/2000 | Berthon-Jones |
| 6,039,044 A | 3/2000 | Sullivan |
| D423,096 S | 4/2000 | Kwok |
| 6,044,844 A | 4/2000 | Kwok et al. |

(56) References Cited

U.S. PATENT DOCUMENTS

| | | |
|---|---|---|
| 6,062,221 A | 5/2000 | Brostrom et al. |
| 6,082,360 A | 7/2000 | Rudolph et al. |
| 6,086,118 A | 7/2000 | McNaughton et al. |
| 6,091,973 A | 7/2000 | Colla et al. |
| D428,987 S | 8/2000 | Kwok |
| 6,095,996 A | 8/2000 | Steer et al. |
| 6,098,205 A | 8/2000 | Schwartz et al. |
| 6,102,040 A | 8/2000 | Tayebi et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,139,787 A | 10/2000 | Harrison |
| 6,152,137 A | 11/2000 | Schwartz et al. |
| 6,155,253 A | 12/2000 | Gamberini |
| 6,192,886 B1 | 2/2001 | Rudolph |
| 6,193,914 B1 | 2/2001 | Harrison |
| D439,326 S | 3/2001 | Hecker et al. |
| 6,196,223 B1 | 3/2001 | Belfer et al. |
| 6,211,263 B1 | 4/2001 | Cinelli et al. |
| 6,213,125 B1 | 4/2001 | Reese et al. |
| 6,231,548 B1 | 5/2001 | Bassett |
| D443,355 S | 6/2001 | Gunaratnam et al. |
| 6,241,930 B1 | 6/2001 | Harrison |
| 6,257,237 B1 | 7/2001 | Suzuki |
| 6,257,626 B1 | 7/2001 | Campau |
| 6,258,066 B1 | 7/2001 | Urich |
| 6,279,573 B1 | 8/2001 | Johnson et al. |
| 6,295,366 B1 | 9/2001 | Baller et al. |
| 6,328,031 B1 | 12/2001 | Tischer et al. |
| 6,328,038 B1 | 12/2001 | Kessler et al. |
| 6,340,024 B1 | 1/2002 | Brookman et al. |
| 6,341,606 B1 | 1/2002 | Bordewick et al. |
| 6,345,618 B1 | 2/2002 | Hayek |
| 6,347,631 B1 | 2/2002 | Hansen et al. |
| 6,357,440 B1 | 3/2002 | Hansen et al. |
| 6,357,441 B1 | 3/2002 | Kwok et al. |
| 6,358,279 B1 | 3/2002 | Tahi et al. |
| 6,371,110 B1 | 4/2002 | Peterson et al. |
| 6,374,826 B1 | 4/2002 | Gunaratnam et al. |
| 6,388,640 B1 | 5/2002 | Chigira et al. |
| 6,397,847 B1 | 6/2002 | Scarberry et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,418,928 B1 | 7/2002 | Bordewick et al. |
| 6,419,660 B1 | 7/2002 | Russo |
| 6,422,238 B1 | 7/2002 | Lithgow |
| 6,423,036 B1 | 7/2002 | Van Huzen |
| 6,425,395 B1 | 7/2002 | Brewer et al. |
| 6,427,694 B1 | 8/2002 | Hecker et al. |
| 6,431,172 B1 | 8/2002 | Bordewick |
| 6,434,796 B1 | 8/2002 | Speirs |
| 6,439,230 B1 | 8/2002 | Gunaratnam et al. |
| 6,439,234 B1 | 8/2002 | Curti et al. |
| 6,448,303 B1 | 9/2002 | Paul |
| 6,463,931 B1 | 10/2002 | Kwok et al. |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| D468,823 S | 1/2003 | Smart |
| 6,513,526 B2 | 2/2003 | Kwok et al. |
| 6,520,182 B1 | 2/2003 | Gunaratnam |
| 6,530,373 B1 | 3/2003 | Patron |
| 6,532,961 B1 | 3/2003 | Kwok et al. |
| 6,536,435 B1 | 3/2003 | Fecteau et al. |
| 6,557,556 B2 | 5/2003 | Kwok et al. |
| 6,561,188 B1 | 5/2003 | Ellis |
| 6,561,190 B1 | 5/2003 | Kwok |
| 6,561,191 B1 | 5/2003 | Kwok |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,601 B2 | 6/2003 | Ziaee |
| 6,581,602 B2 | 6/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,615,830 B1 | 9/2003 | Serowski et al. |
| 6,615,832 B1 | 9/2003 | Chen |
| 6,626,177 B1 | 9/2003 | Ziaee |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,651,663 B2 | 11/2003 | Barnett et al. |
| D484,237 S | 12/2003 | Lang et al. |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,261 B2 | 1/2004 | Lithgow |
| 6,679,265 B2 | 1/2004 | Strickland et al. |
| 6,691,707 B1 | 2/2004 | Gunaratnam et al. |
| 6,691,708 B2 | 2/2004 | Kwok et al. |
| 6,701,535 B2 | 3/2004 | Dobbie et al. |
| 6,701,926 B2 | 3/2004 | Olsen et al. |
| 6,701,927 B2 | 3/2004 | Kwok et al. |
| 6,710,099 B2 | 3/2004 | Cinelli et al. |
| 6,712,072 B1 | 3/2004 | Lang |
| 6,729,333 B2 | 5/2004 | Barnett et al. |
| D492,992 S | 7/2004 | Guney et al. |
| D493,521 S | 7/2004 | Guney |
| 6,766,800 B2 | 7/2004 | Chu et al. |
| 6,766,817 B2 | 7/2004 | da Silva |
| 6,772,760 B2 | 8/2004 | Frater et al. |
| 6,776,162 B2 | 8/2004 | Wood |
| 6,776,163 B2 | 8/2004 | Dougill et al. |
| 6,789,543 B2 | 9/2004 | Cannon |
| 6,796,308 B2 | 9/2004 | Gunaratnam et al. |
| 6,805,117 B1 | 10/2004 | Ho et al. |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B1 | 12/2004 | Fini |
| 6,851,425 B2 | 2/2005 | Jaffre |
| 6,851,428 B2 | 2/2005 | Dennis |
| 6,851,429 B2 | 2/2005 | Bishop |
| 6,860,269 B2 | 3/2005 | Kwok et al. |
| 6,860,270 B2 | 3/2005 | Sniadach |
| 6,871,649 B2 | 3/2005 | Kwok et al. |
| 6,895,965 B2 | 5/2005 | Scarberry et al. |
| 6,907,882 B2 | 6/2005 | Ging |
| 6,914,091 B2 | 7/2005 | Donald et al. |
| 6,918,404 B2 | 7/2005 | Dias da Silva |
| 6,926,004 B2 | 8/2005 | Schumacher |
| 6,938,620 B2 | 9/2005 | Payne, Jr. |
| 6,959,710 B2 | 11/2005 | Barnett et al. |
| 6,968,844 B2 | 11/2005 | Liland et al. |
| 6,972,003 B2 | 12/2005 | Bierman et al. |
| 6,986,352 B2 | 1/2006 | Frater et al. |
| 6,997,177 B2 | 2/2006 | Wood |
| 7,000,614 B2 | 2/2006 | Lang et al. |
| 7,007,696 B2 | 3/2006 | Palkon et al. |
| 7,011,090 B2 | 3/2006 | Drew et al. |
| 7,018,362 B2 | 3/2006 | Bierman et al. |
| 7,040,321 B2 | 5/2006 | Goebel |
| 7,047,972 B2 | 5/2006 | Ging et al. |
| 7,052,127 B2 | 5/2006 | Harrison |
| 7,059,326 B2 | 6/2006 | Heidmann et al. |
| 7,066,179 B2 | 6/2006 | Eaton et al. |
| 7,066,586 B2 | 6/2006 | da Silva |
| 7,069,932 B2 | 7/2006 | Eaton et al. |

(56) References Cited

U.S. PATENT DOCUMENTS

| | | |
|---|---|---|
| 7,076,282 B2 | 7/2006 | Munro et al. |
| 7,076,822 B2 | 7/2006 | Pearce |
| 7,080,645 B2 | 7/2006 | Genger et al. |
| 7,093,599 B2 | 8/2006 | Chen |
| 7,100,610 B2 | 9/2006 | Biener et al. |
| 7,101,359 B2 | 9/2006 | Kline et al. |
| 7,107,989 B2 | 9/2006 | Frater et al. |
| 7,114,497 B2 | 10/2006 | Aylsworth et al. |
| 7,146,976 B2 | 12/2006 | McKown |
| 7,152,599 B2 | 12/2006 | Thomas |
| 7,152,601 B2 | 12/2006 | Barakat et al. |
| 7,178,525 B2 | 2/2007 | Matula, Jr. et al. |
| 7,185,652 B2 | 3/2007 | Gunaratnam et al. |
| 7,191,781 B2 | 3/2007 | Wood |
| 7,207,328 B1 | 4/2007 | Altemus |
| 7,207,335 B2 | 4/2007 | Kwok et al. |
| 7,210,481 B1 | 5/2007 | Lovell et al. |
| 7,216,647 B2 | 5/2007 | Lang et al. |
| 7,234,466 B2 | 6/2007 | Kwok et al. |
| 7,237,551 B2 | 7/2007 | Ho et al. |
| 7,243,723 B2 | 7/2007 | Surjaatmadja |
| D550,836 S | 9/2007 | Chandran et al. |
| D552,733 S | 10/2007 | Criscuolo et al. |
| 7,285,255 B2 | 10/2007 | Kadlec et al. |
| 7,290,546 B2 | 11/2007 | Sprinkle et al. |
| 7,302,950 B2 | 12/2007 | Berthon-Jones et al. |
| 7,308,895 B2 | 12/2007 | Wixey et al. |
| 7,318,439 B2 | 1/2008 | Raje et al. |
| 7,341,060 B2 | 3/2008 | Ging et al. |
| 7,353,826 B2 | 4/2008 | Sleeper et al. |
| 7,357,136 B2 | 4/2008 | Ho et al. |
| 7,441,618 B2 | 10/2008 | Sorg |
| 7,461,656 B2 | 12/2008 | Gunaratnam et al. |
| 7,470,256 B2 | 12/2008 | Lampropoulos et al. |
| 7,481,220 B2 | 1/2009 | Meyer et al. |
| 7,487,772 B2 | 2/2009 | Ging et al. |
| 7,500,480 B2 | 3/2009 | Matula, Jr. et al. |
| 7,503,327 B2 | 3/2009 | Gunaratnam |
| 7,509,958 B2 | 3/2009 | Amarasinghe et al. |
| 7,520,869 B2 | 4/2009 | Lampropoulos et al. |
| 7,523,754 B2 | 4/2009 | Lithgow |
| 7,562,658 B2 | 7/2009 | Madaus et al. |
| 7,597,100 B2 | 10/2009 | Ging et al. |
| 7,610,916 B2 | 11/2009 | Kwok et al. |
| 7,614,400 B2 | 11/2009 | Lithgow et al. |
| 7,614,401 B2 | 11/2009 | Thompson |
| 7,621,274 B2 | 11/2009 | Sprinkle et al. |
| 7,624,735 B2 | 12/2009 | Ho et al. |
| 7,640,934 B2 | 1/2010 | Zollinger et al. |
| 7,654,263 B2 | 2/2010 | Lang et al. |
| 7,658,189 B2 | 2/2010 | Davidson et al. |
| 7,665,464 B2 | 2/2010 | Kopacko et al. |
| 7,699,808 B2 | 4/2010 | Marrs et al. |
| 7,703,457 B2 | 4/2010 | Barnett et al. |
| 7,708,017 B2 | 5/2010 | Davidson |
| 7,743,767 B2 | 6/2010 | Ging et al. |
| 7,762,259 B2 | 7/2010 | Gunaratnam |
| 7,775,209 B2 | 8/2010 | Biener et al. |
| 7,779,832 B1 | 8/2010 | Ho |
| 7,798,144 B2 | 9/2010 | Kwok et al. |
| 7,814,911 B2 | 10/2010 | Bordewick et al. |
| 7,819,119 B2 | 10/2010 | Ho |
| 7,827,990 B1 | 11/2010 | Melidis et al. |
| 7,841,345 B2 | 11/2010 | Guney et al. |
| 7,856,980 B2 | 12/2010 | Lang et al. |
| 7,856,982 B2 | 12/2010 | Matula, Jr. et al. |
| 7,861,714 B2 | 1/2011 | Smart |
| 7,861,715 B2 | 1/2011 | Jones et al. |
| 7,874,291 B2 | 1/2011 | Ging et al. |
| 7,874,293 B2 | 1/2011 | Gunaratnam et al. |
| 7,878,199 B2 | 2/2011 | Ging et al. |
| 7,900,631 B2 | 3/2011 | Persson |
| 7,900,635 B2 | 3/2011 | Gunaratnam et al. |
| 7,931,024 B2 | 4/2011 | Ho et al. |
| 7,938,116 B2 | 5/2011 | Ging et al. |
| 7,942,148 B2 | 5/2011 | Davidson et al. |
| 7,942,150 B2 | 5/2011 | Guney et al. |
| 7,958,893 B2 | 6/2011 | Lithgow et al. |
| 7,967,013 B2 | 6/2011 | Ging et al. |
| 7,967,014 B2 | 6/2011 | Heidmann et al. |
| 7,971,590 B2 | 7/2011 | Frater et al. |
| 7,992,559 B2 | 8/2011 | Lang et al. |
| 7,997,267 B2 | 8/2011 | Ging et al. |
| 8,025,057 B2 | 9/2011 | Ging et al. |
| 8,042,538 B2 | 10/2011 | Ging et al. |
| 8,042,541 B2 | 10/2011 | Amarasinghe et al. |
| 8,042,542 B2 | 10/2011 | Ging et al. |
| 8,042,546 B2 | 10/2011 | Gunaratnam et al. |
| 8,051,850 B2 | 11/2011 | Kwok et al. |
| 8,091,553 B2 | 1/2012 | Bordewick et al. |
| 8,096,301 B2 | 1/2012 | Smith et al. |
| 8,136,524 B2 | 3/2012 | Ging et al. |
| 8,136,525 B2 | 3/2012 | Lubke et al. |
| 8,186,348 B2 | 5/2012 | Kwok et al. |
| 8,186,352 B2 | 5/2012 | Gunaratnam et al. |
| 8,210,180 B2 | 7/2012 | Gunaratnam |
| 8,220,459 B2 | 7/2012 | Davidson et al. |
| 8,286,636 B2 | 10/2012 | Gunaratnam et al. |
| 8,312,881 B2 | 11/2012 | Gunaratnam et al. |
| 8,312,883 B2 | 11/2012 | Gunaratnam et al. |
| 8,353,294 B2 | 1/2013 | Frater et al. |
| 8,371,301 B2 | 2/2013 | Biener et al. |
| 8,402,972 B2 | 3/2013 | Lang et al. |
| 2001/0020474 A1 | 9/2001 | Hecker et al. |
| 2002/0020416 A1 | 2/2002 | Namey |
| 2002/0029780 A1 | 3/2002 | Frater et al. |
| 2002/0046755 A1 | 4/2002 | Devoss |
| 2002/0066452 A1 | 6/2002 | Kessler et al. |
| 2002/0069872 A1 | 6/2002 | Gradon et al. |
| 2002/0124849 A1 | 9/2002 | Billette de Villemeur |
| 2002/0143296 A1 | 10/2002 | Russo |
| 2002/0157673 A1 | 10/2002 | Kessler et al. |
| 2003/0062048 A1 | 4/2003 | Gradon et al. |
| 2003/0089373 A1 | 5/2003 | Gradon et al. |
| 2003/0168063 A1 | 9/2003 | Gambone et al. |
| 2003/0196656 A1 | 10/2003 | Moore et al. |
| 2004/0094157 A1 | 5/2004 | Dantanarayana et al. |
| 2004/0106891 A1 | 6/2004 | Langan et al. |
| 2004/0111104 A1 | 6/2004 | Schein et al. |
| 2004/0112384 A1 | 6/2004 | Lithgow et al. |
| 2004/0112385 A1 | 6/2004 | Drew et al. |
| 2004/0118406 A1 | 6/2004 | Lithgow et al. |
| 2004/0127856 A1 | 7/2004 | Johnson |
| 2004/0134497 A1 | 7/2004 | Gunaratnam et al. |
| 2004/0177850 A1 | 9/2004 | Gradon et al. |
| 2004/0211428 A1 | 10/2004 | Jones |
| 2004/0226566 A1 | 11/2004 | Gunaratnam et al. |
| 2004/0255949 A1 | 12/2004 | Lang et al. |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne, Jr. |
| 2005/0098183 A1 | 5/2005 | Nash et al. |
| 2005/0150495 A1 | 7/2005 | Rittner et al. |
| 2005/0211252 A1 | 9/2005 | Lang et al. |
| 2006/0042629 A1 | 3/2006 | Geist |
| 2006/0118117 A1 | 6/2006 | Berthon-Jones et al. |
| 2006/0124131 A1 | 6/2006 | Chandran et al. |
| 2006/0174887 A1 | 8/2006 | Chandran et al. |
| 2006/0207597 A1 | 9/2006 | Wright |
| 2006/0213520 A1 | 9/2006 | Frater et al. |
| 2006/0219246 A1 | 10/2006 | Dennis |
| 2006/0254593 A1 | 11/2006 | Chang |
| 2006/0272646 A1 | 12/2006 | Ho et al. |
| 2006/0283461 A1 | 12/2006 | Lubke et al. |
| 2007/0044804 A1 | 3/2007 | Matula, Jr. et al. |
| 2007/0137653 A1 | 6/2007 | Wood |
| 2007/0215161 A1 | 9/2007 | Frater et al. |
| 2007/0272249 A1 | 11/2007 | Chandran et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0047560 A1 | 2/2008 | Veliss et al. |
| 2008/0060649 A1 | 3/2008 | Veliss et al. |

(56) References Cited

U.S. PATENT DOCUMENTS

| | | | |
|---|---|---|---|
| 2008/0065022 | A1 | 3/2008 | Kyvik et al. |
| 2008/0092906 | A1 | 4/2008 | Gunaratnam et al. |
| 2008/0110469 | A1 | 5/2008 | Weinberg |
| 2008/0178875 | A1 | 7/2008 | Henry |
| 2008/0200880 | A1 | 8/2008 | Kyvik et al. |
| 2008/0257354 | A1 | 10/2008 | Davidson et al. |
| 2008/0276937 | A1 | 11/2008 | Davidson et al. |
| 2008/0314389 | A1 | 12/2008 | Thomas et al. |
| 2009/0044808 | A1 | 2/2009 | Guney et al. |
| 2009/0050156 | A1 | 2/2009 | Ng et al. |
| 2009/0126739 | A1 | 5/2009 | Ng et al. |
| 2009/0139526 | A1 | 6/2009 | Melidis et al. |
| 2009/0139527 | A1 | 6/2009 | Ng et al. |
| 2009/0173343 | A1 | 7/2009 | Omura et al. |
| 2009/0217929 | A1 | 9/2009 | Kwok et al. |
| 2009/0223518 | A1 | 9/2009 | Kwok et al. |
| 2009/0223521 | A1 | 9/2009 | Howard et al. |
| 2010/0000534 | A1 | 1/2010 | Kooij et al. |
| 2010/0000543 | A1 | 1/2010 | Berthon-Jones et al. |
| 2010/0018534 | A1 | 1/2010 | Veliss et al. |
| 2010/0132717 | A1 | 6/2010 | Davidson et al. |
| 2010/0192955 | A1 | 8/2010 | Biener et al. |
| 2010/0229869 | A1 | 9/2010 | Ging et al. |
| 2010/0282265 | A1 | 11/2010 | Melidis et al. |
| 2010/0300447 | A1 | 12/2010 | Biener et al. |
| 2010/0319700 | A1 | 12/2010 | Ng et al. |
| 2011/0030692 | A1 | 2/2011 | Jones et al. |
| 2011/0056497 | A1 | 3/2011 | Scheiner et al. |
| 2011/0162655 | A1 | 7/2011 | Gunaratnam et al. |
| 2011/0220110 | A1 | 9/2011 | Frater et al. |
| 2011/0220114 | A1 | 9/2011 | Lithgow et al. |
| 2011/0226254 | A1 | 9/2011 | Lang et al. |
| 2011/0259337 | A1 | 10/2011 | Hitchcock et al. |
| 2011/0265791 | A1 | 11/2011 | Ging et al. |
| 2012/0017912 | A1 | 1/2012 | Ging et al. |
| 2012/0024291 | A1 | 2/2012 | Amarasinghe et al. |
| 2012/0138063 | A1 | 6/2012 | Eves et al. |
| 2012/0174928 | A1 | 7/2012 | Raje et al. |
| 2012/0222681 | A1 | 9/2012 | Kwok et al. |
| 2012/0266886 | A1 | 10/2012 | Davidson et al. |

FOREIGN PATENT DOCUMENTS

| | | |
|---|---|---|
| AU | 95/16178 | 7/1995 |
| AU | 94/59430 | 10/1995 |
| AU | 95/32914 | 2/1996 |
| AU | 96/51130 | 10/1996 |
| AU | 97/41018 | 4/1998 |
| AU | 98/89312 | 1/1999 |
| AU | 2005100738 | 11/2005 |
| CA | 618807 | 4/1961 |
| CA | 623129 | 7/1961 |
| CA | 1039144 | 9/1978 |
| CN | 1219883 | 6/1999 |
| CN | 2464353 | 12/2001 |
| CN | 1735439 | 2/2006 |
| DE | 185 017 | 5/1907 |
| DE | 284 800 | 11/1913 |
| DE | 459 104 | 4/1928 |
| DE | 701 690 | 1/1941 |
| DE | 30 11 900 | 10/1980 |
| DE | 146 688 | 1/1981 |
| DE | 30 15 279 | 10/1981 |
| DE | 31 49 449 | 10/1982 |
| DE | 159 396 | 3/1983 |
| DE | 33 45 067 | 6/1984 |
| DE | 37 07 952 | 3/1987 |
| DE | 35 37 507 | 4/1987 |
| DE | 35 39 073 | 5/1987 |
| DE | 37 19 009 | 12/1988 |
| DE | 39 27 038 | 2/1991 |
| DE | 40 04 157 | 4/1991 |
| DE | 42 12 259 | 1/1993 |
| DE | 42 33 448 | 4/1993 |
| DE | 43 43 205 | 6/1995 |
| DE | 195 48 380 | 7/1996 |
| DE | 196 03 949 | 8/1997 |
| DE | 297 15 718 | 10/1997 |
| DE | 197 35 359 | 1/1998 |
| DE | 297 23 101 | 7/1998 |
| DE | 197 03 526 | 8/1998 |
| DE | 298 10 846 | 8/1998 |
| DE | 198 17 332 | 1/1999 |
| DE | 198 07 961 | 8/1999 |
| DE | 198 08 105 | 9/1999 |
| DE | 198 40 760 | 3/2000 |
| DE | 200 05 346 | 5/2000 |
| DE | 299 23 141 | 5/2000 |
| DE | 200 17 940 | 2/2001 |
| DE | 199 44 242 | 3/2001 |
| DE | 199 54 517 | 6/2001 |
| DE | 100 02 571 | 7/2001 |
| DE | 199 62 515 | 7/2001 |
| DE | 100 45 183 | 5/2002 |
| DE | 102 13 905 | 10/2002 |
| DE | 10 2004 055 433 | 11/2004 |
| DE | 103 31 837 | 1/2005 |
| DE | 20 2004 018 108 | 2/2005 |
| DE | 103 38 169 | 3/2005 |
| EP | 0 054 154 | 6/1982 |
| EP | 0 252 052 | 1/1988 |
| EP | 0 264 772 | 4/1988 |
| EP | 0 288 937 | 11/1988 |
| EP | 0 334 555 | 9/1989 |
| EP | 0 386 605 | 9/1990 |
| EP | 0 427 474 | 5/1991 |
| EP | 0 462 701 | 12/1991 |
| EP | 0 466 960 | 1/1992 |
| EP | 0 303 090 B1 | 4/1992 |
| EP | 0 549 299 | 6/1993 |
| EP | 0 602 424 | 6/1994 |
| EP | 0 608 684 | 8/1994 |
| EP | 0 658 356 | 6/1995 |
| EP | 0 697 225 | 2/1996 |
| EP | 0 178 925 A2 | 4/1996 |
| EP | 0 747 078 | 12/1996 |
| EP | 0 776 679 | 6/1997 |
| EP | 0 821 978 | 2/1998 |
| EP | 0 853 962 | 7/1998 |
| EP | 1 027 905 | 8/2000 |
| EP | 1 057 494 | 12/2000 |
| EP | 1 099 452 | 5/2001 |
| EP | 1 118 346 | 7/2001 |
| EP | 1 163 923 | 12/2001 |
| EP | 1 205 205 | 5/2002 |
| EP | 1 258 266 | 11/2002 |
| EP | 1 334 742 | 8/2003 |
| EP | 1 356 841 | 10/2003 |
| EP | 1 356 843 | 10/2003 |
| EP | 1 360 971 | 11/2003 |
| EP | 1 481 702 | 12/2004 |
| EP | 2 471 566 | 7/2012 |
| EP | 2 471 567 | 7/2012 |
| FR | 780018 | 4/1935 |
| FR | 2 574 657 | 6/1986 |
| FR | 2 658 725 | 8/1991 |
| FR | 2 720 280 | 12/1995 |
| FR | 2 749 176 | 12/1997 |
| FR | 2 823 122 | 10/2002 |
| GB | 532 214 | 1/1941 |
| GB | 649 689 | 1/1951 |
| GB | 823 887 | 11/1959 |
| GB | 1 395 391 | 5/1975 |
| GB | 1 467 828 | 3/1977 |
| GB | 2 145 335 | 3/1985 |
| GB | 2 147 506 | 5/1985 |
| GB | 2 164 569 | 3/1986 |
| GB | 2 176 404 | 12/1986 |
| GB | 2 186 801 | 8/1987 |
| GB | 2 267 648 | 12/1993 |
| GB | 2 368 533 | 5/2002 |
| GB | 2 385 533 | 5/2003 |
| JP | S39-13991 | 7/1964 |

(56) References Cited

FOREIGN PATENT DOCUMENTS

| | | |
|---|---|---|
| JP | S51-142793 | 11/1976 |
| JP | H03-007173 | 1/1991 |
| JP | H09-216240 | 8/1997 |
| JP | H11-000397 | 1/1999 |
| JP | H11-104256 | 4/1999 |
| JP | H11-508159 | 7/1999 |
| JP | 2000-279520 | 10/2000 |
| JP | 2000-325481 | 11/2000 |
| JP | 2000-515784 | 11/2000 |
| JP | 2002-028240 | 4/2002 |
| JP | 2002-543943 | 12/2002 |
| JP | 2003-175106 | 6/2003 |
| JP | 2003-535657 | 12/2003 |
| JP | 2004-000570 | 1/2004 |
| JP | 2005-337371 | 12/2005 |
| JP | 3802872 | 7/2006 |
| WO | WO 80/01044 | 5/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20392 | 11/1992 |
| WO | WO 92/20395 | 11/1992 |
| WO | WO 93/01854 | 2/1993 |
| WO | WO 93/24169 | 12/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/28207 | 9/1996 |
| WO | WO 96/39206 | 12/1996 |
| WO | WO 97/00092 | 1/1997 |
| WO | WO 97/07847 | 3/1997 |
| WO | WO 97/09090 | 3/1997 |
| WO | WO 97/41911 | 11/1997 |
| WO | WO 98/03145 | 1/1998 |
| WO | WO 98/04310 | 2/1998 |
| WO | WO 98/11930 | 3/1998 |
| WO | WO 98/12965 | 4/1998 |
| WO | WO 98/18514 | 5/1998 |
| WO | WO 98/23305 | 6/1998 |
| WO | WO 98/24499 | 6/1998 |
| WO | WO 98/26829 | 6/1998 |
| WO | WO 98/26830 | 6/1998 |
| WO | WO 98/34665 | 8/1998 |
| WO | WO 98/48878 | 11/1998 |
| WO | WO 99/16327 | 4/1999 |
| WO | WO 99/25410 | 5/1999 |
| WO | WO 99/43375 | 9/1999 |
| WO | WO 99/58181 | 11/1999 |
| WO | WO 99/61088 | 12/1999 |
| WO | WO 99/65554 | 12/1999 |
| WO | WO 00/20072 | 4/2000 |
| WO | WO 00/21600 | 4/2000 |
| WO | WO 00/35525 | 6/2000 |
| WO | WO 00/38772 | 7/2000 |
| WO | WO 00/50121 | 8/2000 |
| WO | WO 00/57942 | 10/2000 |
| WO | WO 00/69521 | 11/2000 |
| WO | WO 00/72905 | 12/2000 |
| WO | WO 00/74758 | 12/2000 |
| WO | WO 00/76568 | 12/2000 |
| WO | WO 00/78381 | 12/2000 |
| WO | WO 00/78384 | 12/2000 |
| WO | WO 01/62326 | 8/2001 |
| WO | WO 01/95965 | 12/2001 |
| WO | WO 01/97892 | 12/2001 |
| WO | WO 01/97893 | 12/2001 |
| WO | WO 02/11804 | 2/2002 |
| WO | WO 02/32491 | 4/2002 |
| WO | WO 02/38221 | 5/2002 |
| WO | WO02/45784 | 6/2002 |
| WO | WO 03/005931 | 1/2003 |
| WO | WO 03/059427 | 7/2003 |
| WO | WO 03/082406 | 10/2003 |
| WO | WO 03/090827 | 11/2003 |
| WO | WO 03/105921 | 12/2003 |
| WO | WO 2004/007010 | 1/2004 |
| WO | WO 2004/022144 | 3/2004 |
| WO | WO 2004/022145 | 3/2004 |
| WO | WO 2004/022146 | 3/2004 |
| WO | WO 2004/022147 | 3/2004 |
| WO | WO 2004/041342 | 5/2004 |
| WO | WO 2004/073778 | 9/2004 |
| WO | WO 2004/078228 | 9/2004 |
| WO | WO 2004/078230 | 9/2004 |
| WO | WO 2004/096332 | 11/2004 |
| WO | WO 2005/002656 | 1/2005 |
| WO | WO 2005/018523 | 3/2005 |
| WO | WO 2005/021075 | 3/2005 |
| WO | WO 2005/028010 | 3/2005 |
| WO | WO 2005/053781 | 6/2005 |
| WO | WO 2005/063326 | 7/2005 |
| WO | WO 2005/063328 | 7/2005 |
| WO | WO 2005/086943 | 9/2005 |
| WO | WO 2005/094928 | 10/2005 |
| WO | WO 2005/099801 | 10/2005 |
| WO | WO 2005/110220 | 11/2005 |
| WO | WO 2005/118040 | 12/2005 |
| WO | WO 2005/123166 | 12/2005 |
| WO | WO 2006/000046 | 1/2006 |
| WO | WO 2006/014630 | 2/2006 |
| WO | WO 2006/052653 | 5/2006 |
| WO | WO 2006/069345 | 6/2006 |
| WO | WO 2006/069415 | 7/2006 |
| WO | WO 2006/074513 | 7/2006 |
| WO | WO 2006/074515 | 7/2006 |
| WO | WO 2006/074516 | 7/2006 |
| WO | WO 2006/099658 | 9/2006 |
| WO | WO 2006/102707 | 10/2006 |
| WO | WO 2006/130903 | 12/2006 |
| WO | WO 2006/138416 | 12/2006 |
| WO | WO 2007/009182 | 1/2007 |
| WO | WO 2007/041751 | 4/2007 |
| WO | WO 2007/041786 | 4/2007 |
| WO | WO 2007/045008 | 4/2007 |
| WO | WO 2007/048174 | 5/2007 |
| WO | WO 2007/053878 | 5/2007 |
| WO | WO 2007/143772 | 12/2007 |
| WO | WO 2007/145534 | 12/2007 |
| WO | WO 2008/011682 | 1/2008 |
| WO | WO 2008/011683 | 1/2008 |
| WO | WO 2008/040050 | 4/2008 |
| WO | WO 2008/070929 | 6/2008 |
| WO | WO 2009/026627 | 3/2009 |
| WO | WO 2009/052560 | 4/2009 |
| WO | WO 2009/062265 | 5/2009 |
| WO | WO 2009/108994 | 9/2009 |
| WO | WO 2009/108995 | 9/2009 |
| WO | WO 2009/109004 | 9/2009 |
| WO | WO 2010/028425 | 3/2010 |
| WO | WO 2010/066004 | 6/2010 |

OTHER PUBLICATIONS

Photograph of Weinmann mask, acquired prior to 1998.
4 additional photographs of Weinmann mask, currently considered before applicants' filing date.
Nellcor Puritan Bennett, "There are a Lot of Noses Out There," dated 1995, pp. 1-12.
ResCare, "Introducing The Sullivan Bubble Mask System—Series 3," 4 pages, currently considered before Applicant's filing date.
ResCare, Sullivan Series 3 Cushions and Frames photographs, 2 pages, currently considered before Applicant's filing date.
ResCare, "The Sullivan—APD 2 Nasal CPAP System," 10 pages, currently considered before Applicant's filing date.
ResCare, "The Sullivan Mask System," 2 pages, currently considered before Applicant's filing date.
ResMed, "Mask Frames," retrieved from www.resmed.com/maskframes/mask.htm, 2 pages, captured Jan. 4, 1997.

(56) References Cited

OTHER PUBLICATIONS

ResMed, "Modular Mask Components," retrieved from http://www.resmed.com/products/standards.htm, 3 pages, captured Dec. 15, 2000.
ResMed, "Nasal Cushions," retrieved from www.resmed.com/cushions/cushions.htm, captured Jan. 4, 1997.
ResMed, "Sullivan Comfort Bi-level System Operating Manual," dated 2000, pp. 1-26.
Adam J. Singer MD et al. "The Cyanoacrylate Topical Skin Adhesives," American Journal of Emergency Medicine, vol. 26, 2008, pp. 490-496.
Australian Appln. No. 2003275762—Examiner's Report No. 3, dated Nov. 18, 2009.
Australian Appln. No. 2005253641—Examiner's First Report, dated Apr. 20, 2010.
Australian Appln. No. 2005253641—Examiner's Report, dated Aug. 18, 2011.
Australian Appln. No. 2006206040—Examination Report, dated Jun. 27, 2012.
Australian Appln. No. 2010251884—Examination Report, dated Jul. 27, 2012.
Chinese Appln. No. 200480011911.9—Office Action (w/English translation), dated Jun. 24, 2010.
Chinese Appln. No. 200580020203.6—Office Action (w/English translation), dated Jun. 1, 2010.
Chinese Appln. No. 200580020203.6—Office Action (w/English translation), dated Jul. 6, 2011.
Chinese Appln. No. 200580020203.6—Office Action (w/English translation), dated Dec. 23, 2011.
Chinese Appln. No. 200580020203.6—Office Action (w/English translation), dated Apr. 18, 2012.
Chinese Appln. No. 200680002169.4—Office Action (w/English translation), dated Mar. 23, 2010.
Chinese Appln. No. 200680002169.4—Third Office Action (w/English translation), dated Nov. 11, 2010.
Chinese Appln. No. 200810109270.0—Office Action (w/English translation), dated Oct. 19, 2011.
Chinese Appln. No. 200810109270.0—Office Action (w/English translation), dated Jun. 27, 2012.
Chinese Appln. No. 200910223650.1—Office Action (w/English translation), dated Mar. 29, 2012.
Chinese Appln. No. 200980116004.3—Office Action (w/English translation), dated Dec. 24, 2012.
Chinese Appln. No. 201010000226.3—Office Action (w/English translation), dated Apr. 26, 2012.
Chinese Appln. No. 201010517066.X—Office Action (w/English translation), dated Nov. 10, 2011.
Chinese Appln. No. 201010517066.X—Office Action (w/English translation), dated Nov. 5, 2012.
ComfortLite™, Respironics, http://comfortlite.respironics.com, before applicants' filing date.
ComfortLite™ 2,Respironics, http://comfortlite2.respironics.com, before applicants' filing date
"Ear Loop Face Mask", before applicants' filing date.
European Appln. No. EP 01944732.5—Office Action, dated Nov. 27, 2009.
European Appl. No. EP 02714190.2—Search Report, dated Jul. 11, 2006.
European Appln No. EP 03793493.2—Supplementary Search Report, dated Dec. 2, 2009.
European Appln. No. EP 03793493.2—Office Action, dated Mar. 18, 2011.
European Appln. No. EP 03810331.3—Supplementary Search Report, dated Dec. 18, 2009.
European Appln. No. EP 04730413.4—Supplementary Search Report, dated Sep. 29, 2009.
European Appln. No. EP 04802114.1—Supplementary Search Report, dated Apr. 27, 2009.
European Appln. No. EP 04802133.1—Supplementary Search Report, dated Sep. 8, 2009.
European Appln. No. EP 04802133.1—Office Action, dated Dec. 22, 2009.
European Appln. No. EP 05746824.1—Supplementary Search Report, dated Dec. 17, 2009.
European Appln. No. EP 05749447.8—Supplementary Search Report, dated Dec. 8, 2009.
European Appln. No. EP 06704287.9—Supplementary Search Report, dated Oct. 6, 2009.
European Appln. No. EP 06704287.9—Office Action, dated Jul. 18, 2011.
European Appln. No. EP 07784697.0—Search Report, dated Jul. 27, 2009.
European Appln. No. EP 07845378.4—Search Report, dated Dec. 1, 2009.
European Appln. No. EP 08154854.7—Extended Search Report, dated Nov. 27, 2008.
European Appln. No. EP 08154854.7—Examination Report, dated Jul. 1, 2011.
European Appln. No. EP 08161249.1—Extended Search Report, dated Mar. 19, 2009.
European Appln .No. EP 08161868.8—Search Report, dated Sep. 23, 2008.
European Appln .No. EP 09003544.5—Search Report, dated Jun. 2, 2009.
European Appln. No. EP 09161984.1—Extended Search Report, dated Sep. 3, 2009.
European Appln. No. EP 09178736.6—Search Report, dated Apr. 19, 2010.
European Appln. No. EP 10181516.5—Search Report, dated Jun. 13, 2012.
European Appln. No. EP 10182015.7—Search Report, dated Jun. 15, 2012.
European Appln. No. EP 11174401.7—Search Report, dated Oct. 20, 2011.
European Appln. No. EP 11174407.4—Extended Search Report, dated Oct. 20, 2011.
European Appln. No. EP 12154923.2—Extended Search Report, dated Jun. 1, 2012.
European Appln. No. EP 12154926.5—Extended Search Report, dated Jun. 6, 2012.
European Appln. No. EP 12165749.8—Extended Search Report, dated Oct. 10, 2012.
European Appln. No. EP 12165751.4—Extended Search Report, dated Oct. 8, 2012.
Fisher and Paykel Col.—Product Family—http://www.fphcare.com/osa/products.asp/, before applicants' filing date.
German Patent No. 101 51 984—Decision from Opposition hearing by Weinmann (w/English translation), dated Dec. 6, 2007.
Hans Rudolph, Inc.—Mask Products—http://www.rudolphkc.com/products.php?category=MASKS, before applicants' filing date.
"If You Hate CPAP! You Need CPAP Pro®," www.cpappro.com, before applicants' filing date
Japanese Appln. No. S52-164619—English translation of Figure 1, Dec. 1977.
Japanese Appln. No. 2003-537718—Office Action (w/English translation), dated Oct. 7, 2008.
Japanese Appln. No. 2003-559587—Office Action (w/English translation), dated Mar. 17, 2009.
Japanese Appln. No. 2005-004072—Office Action (w/English translation), dated Sep. 24, 2009.
Japanese Appln. No. 2005-337371—Reasons for Rejection (w/English translation), dated Feb. 22, 2011.
Japanese Appln. No. 2005-337371—Final Office Action (w/English translation), dated Jan. 31, 2012.
Japanese Appln. No. 2006-504029—Office Action (w/English translation), dated Nov. 10, 2009.
Japanese Appln. No. 2006-545843—Notice of Reasons for Rejection (w/English translation), dated Jun. 7, 2011.
Japanese Appln. No. 2007-515732—Office Action (w/English translation), dated Aug. 24, 2010.
Japanese Appln. No. 2007-515732—Office Action (w/English translation), dated Aug. 16, 2011.

(56) References Cited

OTHER PUBLICATIONS

Japanese Appln. No. 2007-515732—Office Action (w/English translation), dated Jun. 12, 2012.
Japanese Appln. No. 2007-550636—Office Action (w/English translation), dated Mar. 18, 2011.
Japanese Appln. No. 2007-550636—Office Action (w/English translation), dated Mar. 21, 2012.
Japanese Appln. No. 2007-550636—Notice of Allowance, dated Jul. 10, 2012.
Japanese Appln. No. 2009-140433—Office Action (w/English translation), dated Aug. 20, 2011.
Japanese Appln. No. 2009-140433—Notice of Allowance, dated Sep. 4, 2012.
Japanese Appln. No. 2010-195597—Office Action (w/English translation), dated Jun. 12, 2012.
Japanese Appln. No. 2010-214485—Office Action (w/English translation), dated Jun. 12, 2012.
Japanese Appln. No. 2010-268127—Notice of Reasons for Rejection (w/English translation), dated Jul. 10, 2012.
Japanese Appln. No. 2011-038110—Office Action (w/English translation), dated Aug. 14, 2012.
Joel W. Beam, "Tissue Adhesives for Simple Traumatic Lacerations," Journal of Athletic Training, 2008, vol. 43, No. 2, pp. 222-224.
JP 11-000397A Machine Translation, provided by the Japanese Patent Office, Jan. 6, 2009, full document.
Laurent Brochard, "Pressure Support Ventilation," Chapter 9, Part IV—Conventional Methods of Ventilator Support, pp. 239-257, 1994.
Mask 1 Photographs, Respironics Inc., Reusable Full Mask (small) Part #452033 Lot #951108, before applicants' filing date.
Mask 2 Photographs, Puritan—Bennett, Adam Curcuit, Shell Part #231700, Swivel Part #616329-00, Pillows (medium) Part #616324, before applicants' filing date.
Mask 3 Photographs, DeVilbiss Healthcare Inc., Devilbiss Seal-Ring and CPAP Mask Kit (medium), Part #73510-669, before applicants' filing date.
Mask 4 Photographs, Respironics Inc., Monarch Mini Mask with Pressure Port, Part #572004, Monarch Headgear, Part #572011, before applicants' filing date.
Mask 5 Photographs, Healthdyne Technologies, Nasal CPAP Mask (medium narrow), part #702510, before applicants' filing date.
Mask 6 Photographs, Healthdyne Technologies, Soft Series Nasal CPAP Mask, Part #702020, before applicants' filing date.
Mask 7 Photographs, DeVilbiss Healthcare Inc., Small Mask and Seal Rings, Part #73510-668, before applicants' filing date.
Mask 8 Photographs, Respironics Inc., Reusable Contour Mask (medium), Part #302180, before applicants' filing date.
Mask 9 Photographs, Healthdyne Technologies, Healthdyne Large Headgear, before applicants' filing date.
Mask 10 Photographs, Respironics Inc., Soft Cap (medium), Part #302142, before applicants' filing date.
Mask 11 Photographs, Weinmann: Hamburg, Nasalmaskensystem mit Schalldämpfer (medium), Part #WN 23105, before applicants' filing date.
Mask 12 Photographs, Life Care, before applicants' filing date.
Mask 13 Photographs, Healthdyne Technologies, before applicants' filing date.
Mark 14 Photographs, King System, before applicants' filing date.
Mask 15 Photographs, Respironics Inc., Pediatric Mask, before applicants' filing date.
Mask 16 Photographs, Hans Rudolph Inc., Hans Rudolph Silicone Rubber Face Mask/8900, before applicants' filing date.
McPherson et al., "Respiratory Therapy Equipment," Chapter 8, Third Edition, Introduction to Ventilators, pp. 230-253, 1985.
Merriam-Webster Online Dictionary definition of moveable from the 14th century, before applicants' filing date.
New Zealand Appln. No. 539836—Examination Report, dated Aug. 25, 2005.
New Zealand Appln. No. 564877—Examination Report, dated Dec. 2, 2009.
New Zealand Appln. No. 567375—Examination Report, dated Nov. 17, 2009.
New Zealand Appln. No. 587344—Examination Report, dated Jan. 19, 2012.
New Zealand Appln. No. 587344—Examination Report, dated Aug. 3, 2012.
New Zealand Appln. No. 587820—Examination Report, dated Sep. 13, 2010.
New Zealand Appln. No. 597552—Examination Report, dated Jan. 19, 2012.
New Zealand Appln. No. 597689—Examination Report, dated Jan. 25, 2012.
PCT/AU2003/001163—International Search Report, dated Nov. 4, 2003.
PCT/AU2003/001471—International Search Report, dated Feb. 12, 2004.
PCT/AU2004/000563—International Search Report, dated Jun. 23, 2004.
PCT/AU2004/001760—International Search Report, dated Jan. 12, 2005.
PCT/AU2004/001760—International Preliminary Report on Patentability, dated Jul. 3, 2006.
PCT/AU2004/001813—International Search Report, dated Mar. 7, 2005.
PCT/AU2004/001813—International Preliminary Report on Patentability, dated Jul. 3, 2006.
PCT/AU2004/001832—International Search Report, dated Mar. 24, 2005.
PCT/AU2004/001832—International Preliminary Report on Patentability, dated Jul. 3, 2006.
PCT/AU2005/000803—International Search Report, dated Jun. 30, 2005.
PCT/AU2005/000850—International Search Report, dated Aug. 12, 2005.
PCT/AU2005/000850—International Preliminary Report on Patentability, dated Dec. 20, 2006.
PCT/AU2006/000032—International Search Report, dated May 15, 2006.
PCT/AU2006/000032—International Preliminary Report on Patentability, dated Jul. 17, 2007.
PCT/AU2006/000770—International Search Report, dated Aug. 3, 2006.
PCT/AU2006/001570—International Search Report, dated Jan. 5, 2007.
PCT/AU2007/001051—International Search Report, dated Nov. 5, 2007.
PCT/AU2007/001052—International Search Report, dated Oct. 9, 2007.
PCT/AU2007/001456—International Search Report, dated Dec. 12, 2007.
PCT/AU2007/001936—International Search Report, dated Mar. 4, 2008.
PCT/AU2009/000240—International Search Report, dated May 21, 2009.
PCT/AU2009/000241—International Search Report, dated May 18, 2009.
PCT/AU2009/000262—International Search Report, dated Jun. 9, 2009.
PCT/AU2009/001102—International Search Report, dated Dec. 11, 2009.
PCT/AU2009/001144—International Search Report, dated Dec. 8, 2009.
PCT/AU2010/000657—International Search Report, dated Sep. 9, 2010.
Product Brochure for ResMed "Sullivan® Mirage™—The Mirage is Real. A Perfect Fit—First Time,"© 1997 ResMed Limited, 4 pages.
Product Brochure for ResMed "Sullivan® Mirage™—The Mirage is Real. A Perfect Fit—First Time,"© 1998 ResMed Limited, 4 pages.
ResCare, "Sullivan Nasal CPAP Products—Mask Systems Handbook," Sep. 1993.
ResMed Co.—Mask Products—http://resmed.com/portal/site/ResMedUS/index.jsp?, before applicants' filing date.

(56) References Cited

OTHER PUBLICATIONS

ResMed Ltd., "Improving patient compliance with The ResMed Range of Mask Systems The Ultimate Interface for CPAP treatment," before applicants' filing date, 4 pages.

The ResMed Range of Mask Systems, product brochure, Nov. 1995, 4 pages.

ResMed, "ResMed Origins," pp. 1-64, currently considered before Applicant's filing date.

Respironics Co.—Mask Family—http://masksfamily.respironics.com/, before Applicant's filing date.

SNAPP Nasal Interface, Tiara Medical Systems, Inc.—http://tiaramed.com/asp_shops/shopdisplayproducts.asp?id=109&cat=SNAPP%2A+Nasal+Interface, before applicants' filing date.

"Somnomask" brochure, 1999 along with various invoices relating to the "Somnomask".

Somnotron CPAP—Great WM 2300 Instruction Manual, Weinmann Hamburg, 1991, 11 pages.

Subbu Venkatraman et al., "Review Skin Adhesives and Skin Adhesion 1. Transdermal Drug Delivery Systems," Biomaterials, vol. 19, 1998, pp. 1119-1136.

Unsolicited email from Elson Silva, PhD, dated Mar. 28, 2008, "Requesting IDS of US 6,766,817 for patents on fluids moving on porosity by Unsaturated Hydraulic Flow," (email provided in both HTML and plain text format).

U.S. Appl. No. 12/083,779—Office Action including PTO-892 listings, dated Feb. 17, 2012.

U.S. Appl. No. 12/083,779—Office Action including PTO-892 listings, dated Sep. 28, 2012.

U.S. Appl. No. 13/619,666, "Nasal Assembly"—Gunaratnam et al., filed Sep. 14, 2012.

U.S. Appl. No. 13/676,736, "Cushion for Patient Interface"—Davidson et al., filed Nov. 14, 2012.

U.S. Appl. No. 13/676,869, "Cushion for Patient Interface"—Davidson et al., filed Nov. 14, 2012.

U.S. Appl. No. 13/676,925, "Cushion for Patient Interface"—Davidson et al., filed Nov. 14, 2012.

U.S. Appl. No. 13/687,680, "Cushion for Patient Interface"—Davidson et al., filed Nov. 28, 2012.

U.S. Appl. No. 13/688,575, "Cushion for Patient Interface"—Davidson et al., filed Nov. 29, 2012.

U.S. Appl. No. 13/688,619, "Cushion for Patient Interface"—Davidson et al., filed Nov. 29, 2012.

U.S. Appl. No. 13/688,875, "Cushion for Patient Interface"—Davidson et al., filed Nov. 29, 2012.

U.S. Appl. No. 13/688,890, "Cushion for Patient Interface"—Davidson et al., filed Nov. 29, 2012.

U.S. Appl. No. 13/688,931, "Cushion for Patient Interface"—Davidson et al., filed Nov. 29, 2012.

U.S. Appl. No. 13/689,094, "Cushion for Patient Interface"—Davidson et al., filed Nov. 29, 2012.

U.S. Appl. No. 13/689,210, "Cushion for Patient Interface"—Davidson et al., filed Nov. 29, 2012.

U.S. Appl. No. 13/689,211, "Cushion for Patient Interface"—Davidson et al., filed Nov. 29, 2012.

U.S. Appl. No. 13/708,049, "Respiratory Mask Assembly"—Frater et al., filed Dec. 7, 2012.

U.S. Appl. No. 13/745,077, "Mask System"—Ng et al., filed Jan. 18, 2013.

U.S. Appl. No. 13/747,701, "Mask System"—Ng et al., filed Jan. 23, 2013.

U.S. Appl. No. 13/747,772, "Mask System"—Ng et al., filed Jan. 23, 2013.

U.S. Appl. No. 60/424,686, filed Nov. 8, 2002 (expired).

U.S. Appl. No. 60/483,622, filed Jul. 1, 2003 (expired).

U.S. Appl. No. No. 60/533,214, filed Dec. 31, 2003 (expired).

U.S. Appl. No. 60/634,802, filed Dec. 10, 2004 (expired).

U.S. Appl. No. 60/643,121, filed Jan. 12, 2005 (expired).

U.S. Appl. No. 60/645,672, filed Jan. 21, 2005 (expired).

U.S. Appl. No. 60/795,615, filed Apr. 28, 2006 (expired).

U.S. Appl. No. 60/833,841, filed Jul. 28, 2006 (expired).

U.S. Appl. No. 60/835,442, filed Aug. 4, 2006 (expired).

U.S. Appl. No. 60/852,649, filed Oct. 19, 2006 (expired).

U.S. Appl. No. 60/874,968, filed Dec. 15, 2006 (expired).

U.S. Appl. No. 60/907,856, filed Apr. 19, 2007 (expired).

U.S. Appl. No. 60/924,241, filed May 4, 2007 (expired).

U.S. Appl. No. 60/929,393, filed Jun. 25, 2007 (expired).

U.S. Appl. No. 60/935,179, filed Jul. 30, 2007 (expired).

U.S. Appl. No. 60/935,336, filed Aug. 8, 2007 (expired).

U.S. Appl. No. 60/996,160, filed Nov. 5, 2007 (expired).

U.S. Appl. No. 61/006,409, filed Jan. 11, 2008 (expired).

U.S. Appl. No. 61/064,818, filed Mar. 28, 2008 (expired).

U.S. Appl. No. 61/071,512, filed May 2, 2008 (expired).

U.S. Appl. No. 61/213,326, filed May 29, 2009 (expired).

U.S. Appl. No. 61/222,711, filed Jul. 2, 2009 (expired).

U.S. Appl. No. 61/263,175, filed Nov. 20, 2009 (expired).

U.S. Appl. No. 61/272,162, filed Aug. 25, 2009 (expired).

U.S. Appl. No. 61/272,250, filed Sep. 4, 2009 (expired).

Webster's New World Dictionary, Third College Edition 1988, definition for engaged and flexible, before applicants' filing date.

Webster's Third New International Dictionary, 1993, Dictionary definition for adjustable, bendable, and mild steel, before applicants' filing date.

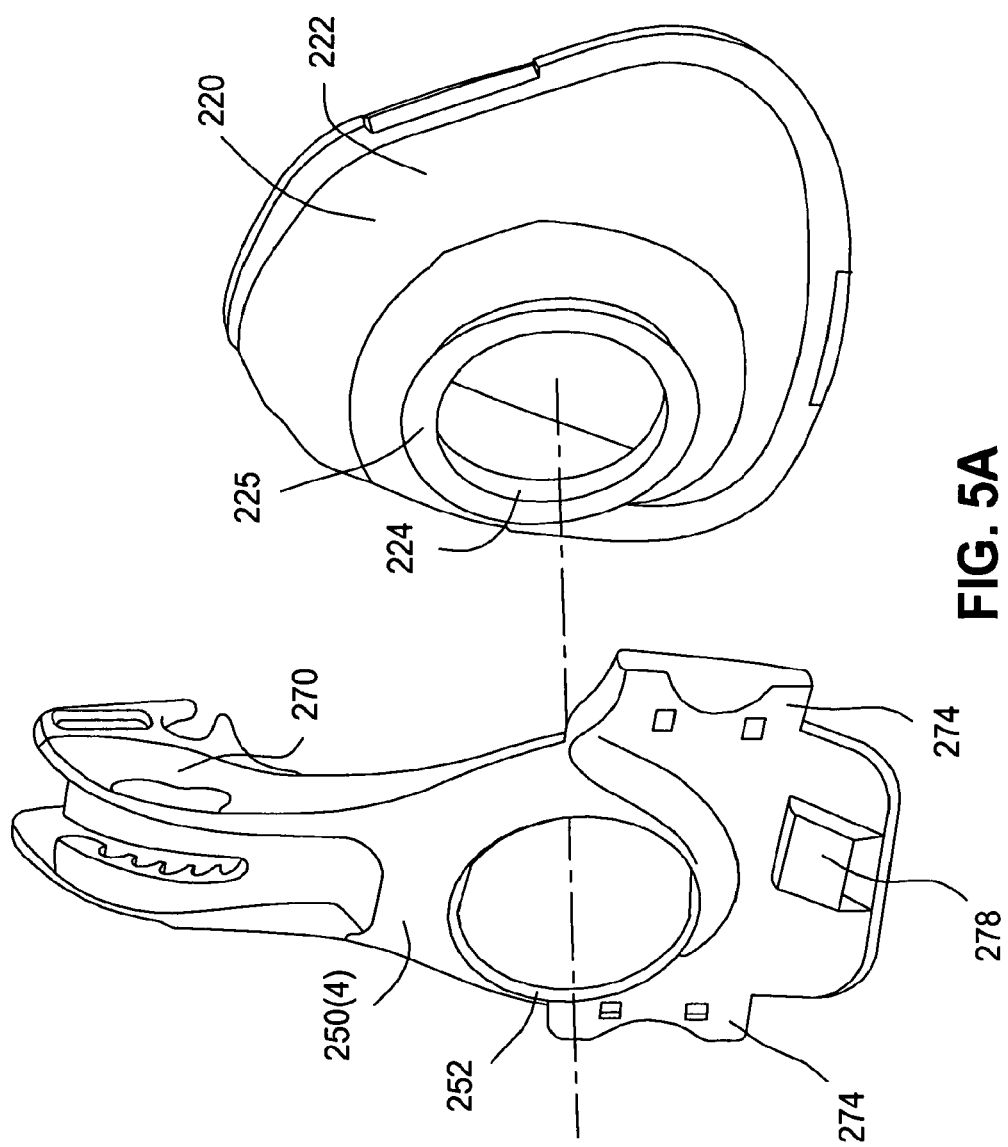

MASK SYSTEM WITH INTERCHANGEABLE HEADGEAR CONNECTORS

CROSS-REFERENCE TO APPLICATION

This is a continuation application of U.S. patent application Ser. No. 12/010,680, filed Jan. 29, 2008, now allowed, which claims the benefit of U.S. Provisional Application No. 60/898,108, filed Jan. 30, 2007, which are incorporated herein by reference in their entirety.

FIELD OF THE INVENTION

The present invention relates to a mask system used for treatment, e.g., of Sleep Disordered Breathing (SDB) with Continuous Positive Airway Pressure (CPAP) or Non-Invasive Positive Pressure Ventilation (NIPPV).

BACKGROUND OF THE INVENTION

Patient interfaces, such as a full-face or nasal mask systems, for use with blowers and flow generators in the treatment of sleep disordered breathing (SDB), typically include a soft face-contacting portion, such as a cushion, and a rigid shell or frame. In use, the interface is held in a sealing position by headgear so as to enable a supply of air at positive pressure (e.g., 2-30 cm $H_2O$) to be delivered to the patient's airways.

One factor in the efficacy of therapy and compliance of patients with therapy is the comfort and fit of the patient interface. It has been necessary to design a wide variety of interfaces to best treat and/or suit the patient's needs. While there are a large number of interfaces, typically each frame has been specifically designed to be used with only a single headgear. That is, only one headgear will work correctly with a given frame due to headgear vectors. This is because the frame will have connection points for the headgear located on the frame, and there is a limited way of routing the headgear off these connection points to achieve correct sealing vectors.

PCT Publication No. WO 02/45784, which is incorporated herein by reference in its entirety, discloses a patient mask assembly including a wire brace which clips to the mask and provides attachment locations for headgear straps in alternative positions to those attachment locations which may be provided by the mask.

The present invention provides alternative arrangements of mask systems to enhance the efficacy of therapy and compliance of patients with therapy.

SUMMARY OF THE INVENTION

One aspect of the invention relates to a mask system that can be adapted for use with a variety of different styles or types of headgear.

Another aspect of the invention relates to a mask system for delivering breathable gas to a patient. The mask system includes a common frame provided without built-in or integral headgear attachment points and at least first and second headgear connectors adapted to be provided to the frame. Each of the at least first and second headgear connectors are adapted to attach headgear straps of headgear. The at least first and second headgear connectors are different from one another in at least one aspect.

Another aspect of the invention relates to a mask system for delivering breathable gas to a patient. The mask system includes at least first and second headgear connectors adapted to attach headgear straps of headgear and a common frame structured to support each of the at least first and second headgear connectors. The at least first and second headgear connectors are different from one another in at least one aspect. Each of the headgear connectors is constructed of a similar material as the frame.

Another aspect of the invention relates to a mask system for delivering breathable gas to a patient. The mask system includes at least first and second headgear connectors adapted to attach headgear straps of headgear and a common frame structured to support each of the at least first and second headgear connectors. The at least first and second headgear connectors are different from one another in at least one aspect. Each of the headgear connectors includes at least one headgear clip receptacle adapted to be engaged with a clip provided to a headgear strap.

Another aspect of the invention relates to a mask system for delivering breathable gas to a patient. The mask system includes at least first and second headgear connectors adapted to attach headgear straps of headgear and a common frame structured to support each of the at least first and second headgear connectors. The at least first and second headgear connectors are different from one another in at least one aspect. The frame includes a central bore adapted to engage an elbow assembly. Each of the headgear connectors includes an opening adapted to removably engage a flange or interfacing structure provided along the central bore of the frame.

Another aspect of the invention relates to a kit including at least first and second headgear connectors adapted to attach headgear straps of headgear, a common frame structured to support each of the at least first and second headgear connectors, a sealing interface or cushion provided to the frame, and at least first and second headgear adapted to attach to a respective one of the at least first and second headgear connectors. The at least first and second headgear connectors are different from one another in at least one aspect.

Another aspect of the invention relates to a method for fitting a mask system to a patient. The method includes providing a common frame without built-in or integral headgear attachment points, selecting headgear based on a preferred headgear style, providing a headgear connector adapted to be provided to the frame and adapted to attach headgear straps of the selected headgear.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 2A to 5B illustrate a common frame with interchangeable headgear connectors for a mask system according to another embodiment of the present invention;

FIGS. 6A to 6D-2 illustrate a common frame with interchangeable headgear connectors for a mask system according to another embodiment of the present invention.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, each single feature or combination of features in any of the embodiments may constitute an additional embodiment.

While each embodiment below is described as including a full-face or nasal interface type, each embodiment may be adapted for use with other suitable interface types. That is, the interface type is merely exemplary, and each embodiment may be adapted to include other interface types, e.g., mouth masks, nasal prongs, etc.

In this specification, the word "comprising" is to be understood in its "open" sense, that is, in the sense of "including", and thus not limited to its "closed" sense, that is the sense of "consisting of". A corresponding meaning is to be attributed to the corresponding words "comprise", "comprised" and "comprises" where they appear.

1. First Embodiment of Common Frame and Interchangeable Headgear Connector

Figure 1A:
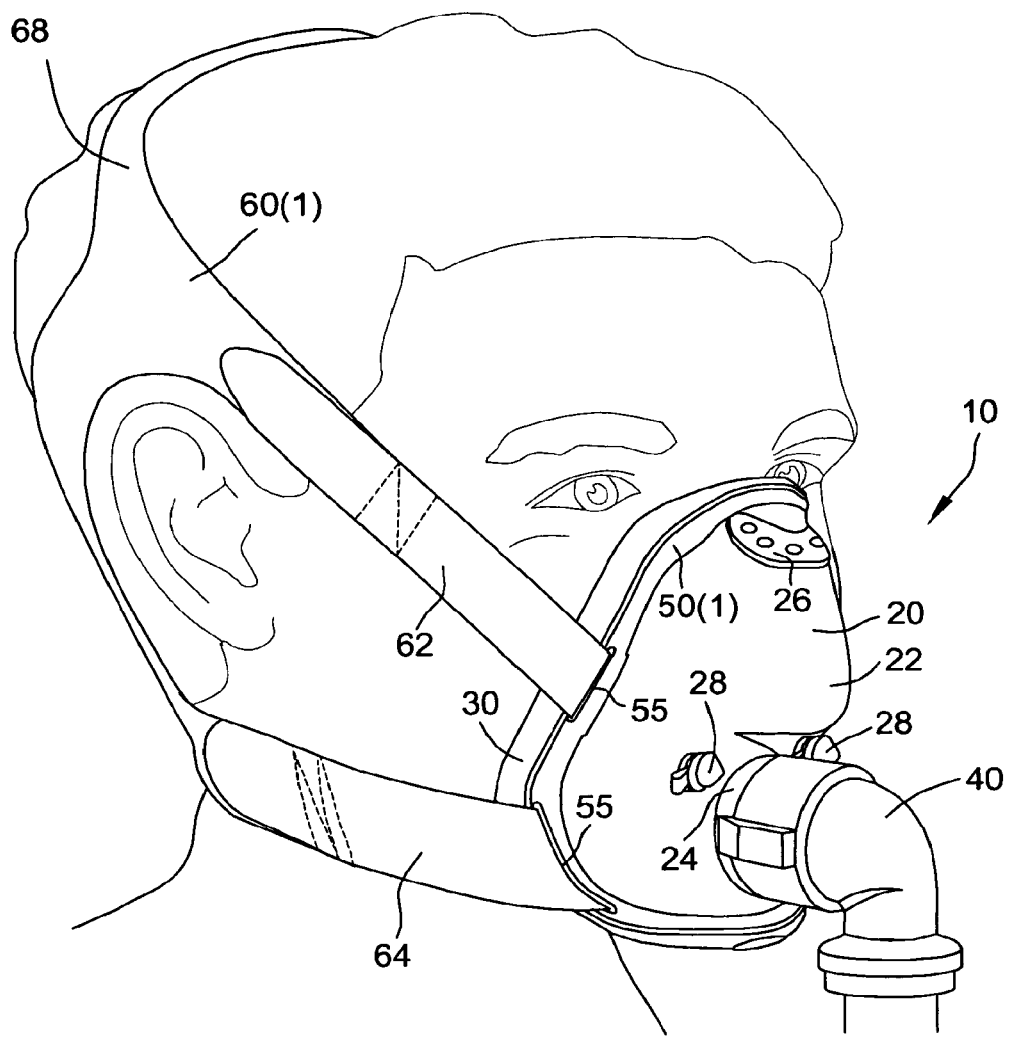
FIGS. 1A- to 1C illustrate a mask system with interchangeable headgear connectors according to an embodiment of the present invention.
Figure 1B:
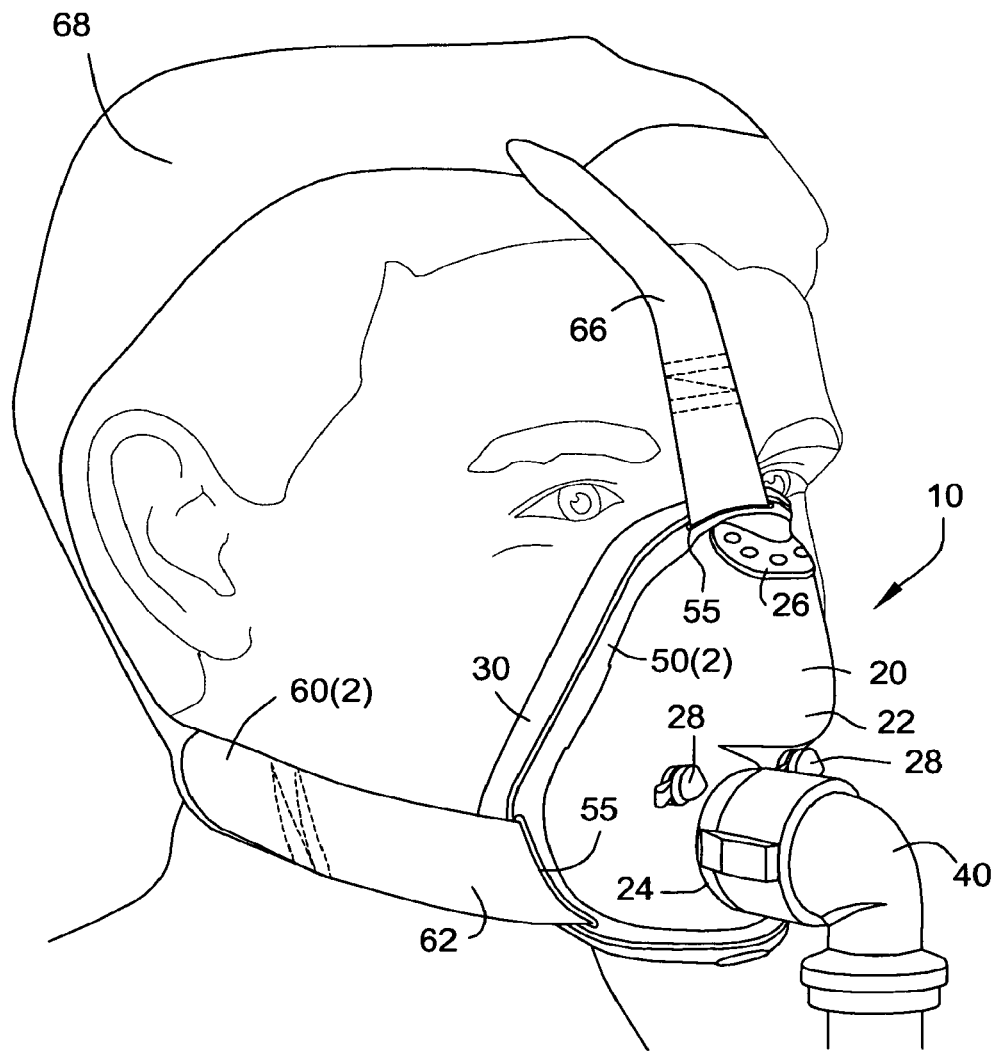
FIGS. 1D-1 to 1D-5 illustrate headgear connectors according to alternative embodiments of the present invention.
Figure 1C:
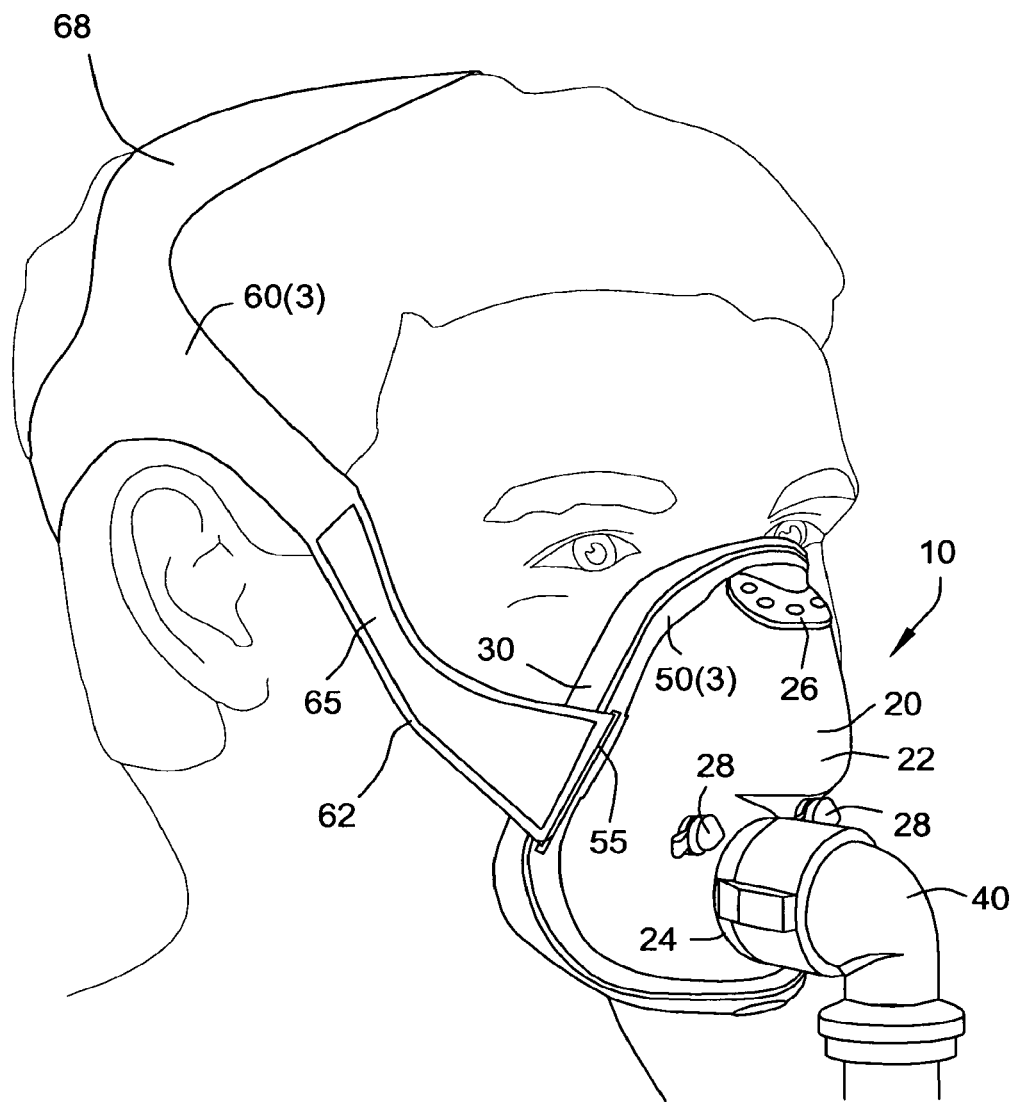

FIGS. 1A to 1C illustrate a mask system 10 including interchangeable headgear connectors according to an embodiment of the present invention. In this embodiment, the mask system 10 includes a full-face interface. The mask system 10 includes a common or universal frame 20, a cushion 30 provided to the frame 20 and adapted to form a seal with the patient's face, an elbow assembly 40 provided to the frame 20 and adapted to be connected to an air delivery tube (not shown) that delivers breathable gas to the patient, one of three headgear connectors 50(1), 50(2), 50(3) removably attachable to the frame 20, and one of three headgear 60(1), 60(2), 60(3) removably attachable a respective one of the headgear connectors 50(1), 50(2), 50(3). This arrangement allows multiple headgear styles to be used with one frame so that different headgear may be mixed and matched with the frame, e.g., depending on patient preference and/or fit. The mask system 10 is intended for use in positive pressure therapy for users with obstructive sleep apnea (OSA) or another respiratory disorder.

The common frame 20 includes a main body 22, a lower bore or annular elbow connection seal 24 adapted to engage the elbow assembly 40, a vent assembly 26 for gas washout, and supplemental ports covered by respective port caps 28. Moreover, the common frame 20 is structured to be selectively and removably coupled to one of three headgear connectors 50(1), 50(2), 50(3) adapted for use with a respective headgear 60(1), 60(2), 60(3). The three headgear 60(1), 60(2), 60(3) may differ in at least one respect from one another such that one may be more suitable or preferable for use with one patient, while another may be more suitable or preferable for use with another patient.

Specifically, the frame 20 includes a ledge or other interfacing structure along its peripheral edge that is adapted to removably connect to each of three different headgear connectors 50(1), 50(2), 50(3) (also referred to as headgear attachment clips). For example, the interfacing structure of the frame 20 may engage each headgear connector 50(1), 50(2), 50(3) with a friction fit, snap-fit, mechanical interlock, or other suitable attachment mechanism. The interfacing structure of the frame 20 does not need to be continuous, but is structured such that multiple headgear connectors can connect thereto.

Each headgear connector 50(1), 50(2), 50(3) includes headgear attachment points 55 along its perimeter that differ in at least one respect from the other headgear connectors. That is, each headgear connector 50(1), 50(2), 50(3) includes different headgear attachment points 55 to allow different style headgear to be used therewith and hence with the frame 20. In the illustrated embodiment, each headgear attachment point 55 is in the form of an opening through which a strap of the headgear may pass and be removably connected. In use, a selected one of the headgear connectors 50(1), 50(2), 50(3) is attached to the frame 20, and headgear 60(1), 60(2), 60(3) having headgear straps associated with such headgear connector 50(1), 50(2), 50(3) is attached to the headgear connector 50(1), 50(2), 50(3) to maintain the mask system 10 in a desired position on the patient's face.

In FIG. 1A, the headgear connector 50(1) includes upper and lower attachment points 55 on each side thereof. As illustrated, this headgear connector 50(1) is structured for use with headgear 60(1) including a pair of upper and lower side straps 62, 64 that are attachable to respective upper and lower attachment points 55 of the headgear connector 50(1). In use, the upper side straps 62 extend over the patient's ears and the lower side straps 64 extend below the patient's ears. The headgear 60(1) also includes a rear portion 68 having straps adapted to cup the occiput of the patient's head in use.

In FIG. 1B, the headgear connector 50(2) includes a side attachment point 55 on each side thereof and a top attachment point 55. As illustrated, this headgear connector 50(2) is structured for use with headgear 60(2) including a pair of side straps 62 that are attachable to respective side attachment points 55 and a top strap 66 that is attachable to the top attachment point 55. In use, the side straps 62 extend below the patient's ears and the top strap extends between the patient's eyes and across the patient's forehead. The headgear 60(2) also includes a rear portion 68 adapted to cup the occiput of the patient's head in use.

In FIG. 1C, the headgear connector 50(3) includes a side attachment point 55 on each side thereof. As illustrated, this headgear connector 50(3) is structured for use with headgear 60(3) including a pair of side straps 62 that are attachable to respective side attachment points 55. In use, the side straps 62 extend over the patient's ears. The headgear 60(3) also includes a rear portion 68 having straps adapted to cup the occiput of the patient's head in use.

As shown in FIG. 1C, each side strap 62 includes a rigidizer 65 to improve stability. The rigidizer 65 may be constructed of a rigid or semi-rigid material, e.g., nylon or plastic, and may be attached to the strap in any suitable manner, e.g., stitching, welding, gluing, or mechanically fixed. It should be appreciated that each headgear style may include one or more straps with a rigidizer to improve stability.

In an embodiment, each headgear connector 50(1), 50(2), 50(3) is constructed of a similar material as the frame 20, e.g., substantially rigid, non-malleable, plastic material (e.g., polycarbonate). However, the headgear connectors and frame may be constructed of other suitable materials.

In an embodiment, the headgear connector may also constitute a cushion clip that is adapted to retain the cushion 30 to the frame 20. For example, the headgear connector may include structure similar to the clip disclosed in U.S. Pat. No. 6,412,487, which is incorporate herein by reference in its entirety. However, it should be appreciated that the cushion 30 may be secured to the frame 20 in other suitable manners.

Figures 1, 1D:
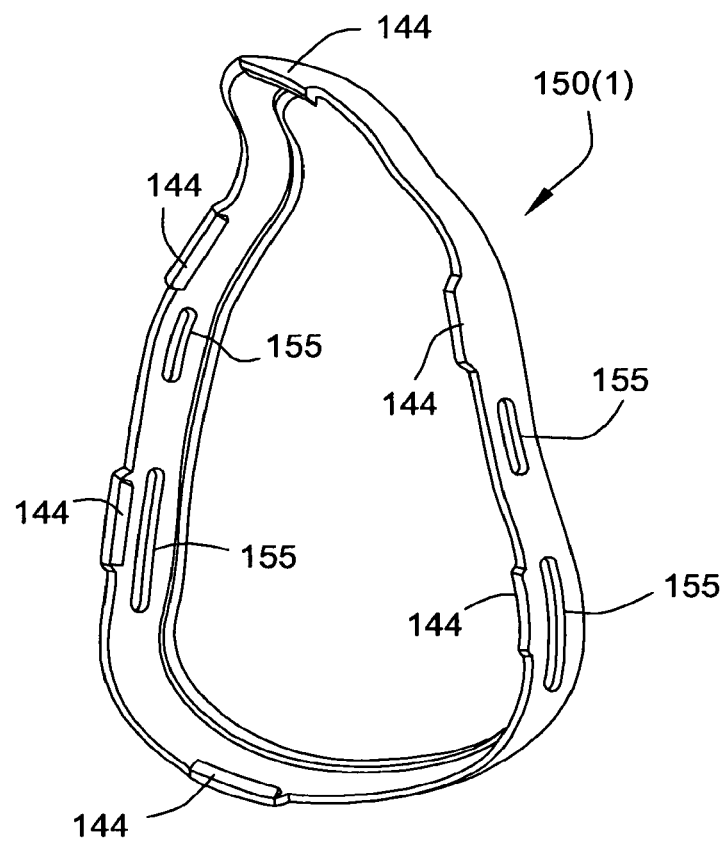

FIGS. 1D-1 to 1D-5 illustrate headgear connectors according to alternative embodiments of the present invention. In FIG. 1D-1, the headgear connector 150(1) is in the form of a cushion clip adapted to retain the cushion 30 to the frame 20.

The headgear connector 150(1) includes a plurality of tabs 144 structured to attach to the frame 20 with a snap-fit. Moreover, the headgear connector 150(1) includes openings 155 through which respective straps of the headgear may pass and be removably connected. As illustrated, the openings 155 are arranged similar to those on the headgear connector 50(1) shown in FIG. 1A.

Figures 1, 1D, 2:
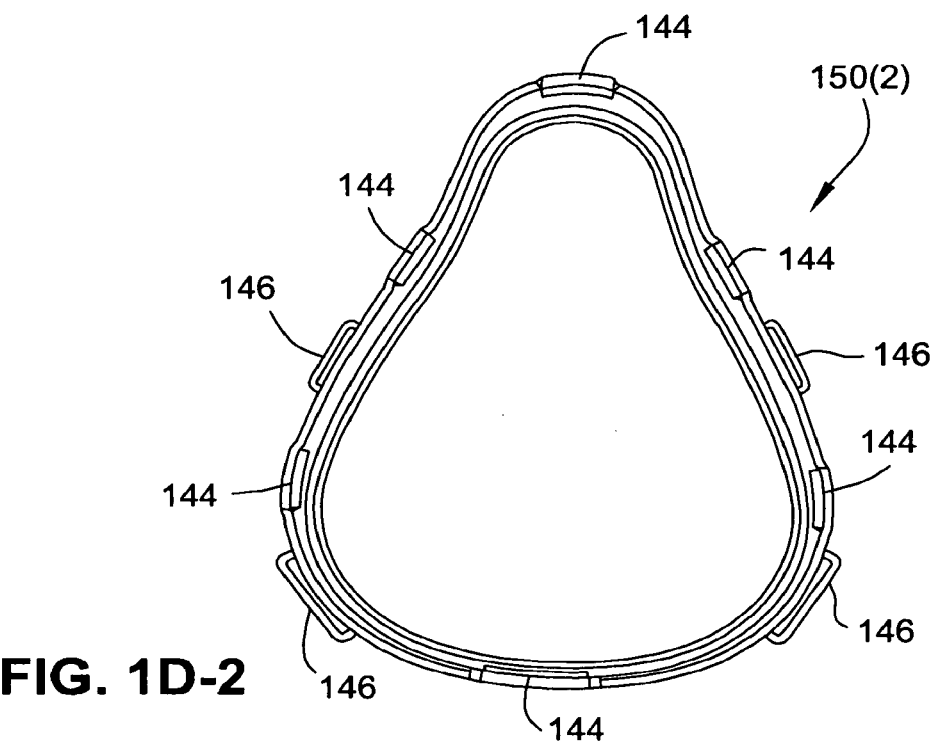

In FIG. 1D-2, the headgear connector 150(2) is in the form of a cushion clip adapted to retain the cushion 30 to the frame 20. The headgear connector 150(2) includes a plurality of tabs 144 structured to attach to the frame 20 with a snap-fit. Moreover, the headgear connector 150(2) includes anchors or cross-bars 146 for attaching respective straps of the headgear. As illustrated, the anchors 146 are arranged similar to the openings on the headgear connector 50(1) shown in FIG. 1A.

In FIG. 1D-3, the headgear connector 150(3) is in the form of a cushion clip adapted to retain the cushion 30 to the frame 20. The headgear connector 150(3) includes a plurality of tabs 144 structured to attach to the frame 20 with a snap-fit. Moreover, the headgear connector 150(3) includes anchors or cross-bars 146 for attaching respective straps of the headgear. As illustrated, the anchors 146 are arranged similar to the openings on the headgear connector 50(2) shown in FIG. 1B.

In FIG. 1D-4, the headgear connector 150(4) is in the form of a cushion clip adapted to retain the cushion 30 to the frame 20. The headgear connector 150(4) includes a plurality of tabs 144 structured to attach to the frame 20 with a snap-fit. Moreover, the headgear connector 150(4) includes anchors or cross-bars 146 for attaching respective straps of the headgear. As illustrated, the anchors 146 are arranged similar to the openings on the headgear connector 50(3) shown in FIG. 1C.

In FIG. 1D-5, the headgear connector 150(5) is in the form of a cushion clip adapted to retain the cushion 30 to the frame 20. The headgear connector 150(5) includes a plurality of tabs 144 structured to attach to the frame 20 with a snap-fit. Moreover, the headgear connector 150(5) includes anchors or cross-bars 146 for attaching respective side straps of the headgear. In addition, the headgear connector 150(5) includes an extension 148 that provides a plurality of openings 149 for attaching one or more upper straps of the headgear.

It should be appreciated that the illustrated headgear 60(1), 60(2), 60(3) are merely exemplary and other headgear arrangements are possible for use with the illustrated headgear connectors. Also, while the mask system is described as including three different headgear connectors for use with respective headgear, it should be appreciated that the mask system may include any suitable number of headgear connectors for use with associated headgear, e.g., at least two headgear connectors.

The common or universal frame 20 is advantageous since it works with a plurality of different headgear via a respective headgear connector, thereby eliminating the need to specifically make the frame for a particular headgear, as is the standard. That is, the mask or frame/cushion/elbow sub-assembly is independent of the headgear, which allows independent selection of the frame/cushion/elbow sub-assembly and the headgear. Therefore, the frame/cushion/elbow sub-assembly may be selected based on the desired mask seal of the patient and the headgear may be selected based on the desired fit or support arrangement. This allows the patient to achieve both a good seal and a secure, comfortable fit, rather than compromising between one or the other, as is typically the case. This arrangement improves comfort, efficacy of treatment, and compliance. In addition, the attachment points provided by the headgear connector are associated with a specific headgear so that correct sealing vectors may be achieved.

In an embodiment, the frame/cushion/elbow sub-assembly may be provided separately from the headgear connector 50(1), 50(2), 50(3) and associated headgear 60(1), 60(2), 60(3) (e.g., sold separately). This arrangement allows the patient to select headgear based on a preferred headgear style, and then be provided with an associated headgear connector for connection to the frame/cushion/elbow sub-assembly.

2. Second Embodiment of Common Frame and Interchangeable Headgear Connector

FIGS. 2A to 5B illustrate a common or universal frame 220 with interchangeable headgear connectors 250(1), 250(2), 250(3), 250(4) for a mask system according to another embodiment of the present invention. In this embodiment, the mask system includes a nasal interface. Similar to the embodiment described above, this arrangement allows multiple headgear styles to be used with one frame so that different headgear may be mixed and matched with the frame, e.g., depending on patient preference and/or fit. In addition, this arrangement allows the use of different accessories, e.g., forehead support.

The common frame 220 includes a main body 222 and a central bore or annular elbow connection seal 224 adapted to engage an elbow assembly. Moreover, the common frame 220 is structured to be selectively and removably coupled to one of multiple headgear connectors 250(1), 250(2), 250(3), 250(4) adapted for use with a respective headgear and/or accessory.

Specifically, the central bore 224 of the frame 220 includes a flange or interfacing structure 225 along its peripheral edge that is adapted to removably connect to each of the multiple headgear connectors 250(1), 250(2), 250(3), 250(4) (also referred to as headgear attachment clips). In the illustrated embodiment, each headgear connector 250(1), 250(2), 250(3), 250(4) includes an opening 252 adapted to engage the interfacing structure 225 with a friction fit, snap-fit, mechanical interlock, or other suitable attachment mechanism. However, other suitable arrangements for attaching each headgear connector to the frame are possible.

Each headgear connector 250(1), 250(2), 250(3), 250(4) includes headgear and/or accessory attachment points along its perimeter that differ in at least one respect from the other headgear connectors. That is, each headgear connector 250(1), 250(2), 250(3), 250(4) includes different headgear and/or accessory attachment points to allow different style headgear and/or accessories to be used therewith and hence with the frame 220. In use, a selected one of the headgear connectors 250(1), 250(2), 250(3), 250(4) is attached to the frame 220, and headgear or accessories associated with such headgear connector 250(1), 250(2), 250(3), 250(4) is attached to the headgear connector 250(1), 250(2), 250(3), 250(4) to maintain the mask system in a desired position on the patient's face.

While the mask system is described as including four different headgear connectors 250(1), 250(2), 250(3), 250(4) for use with respective headgear and/or accessories, it should be appreciated that the mask system may include any suitable number of headgear connectors for use with associated headgear and/or accessories, e.g., at least two headgear connectors.

2.1 Headgear Connector with Adjustable Forehead Support

Figure 2A:
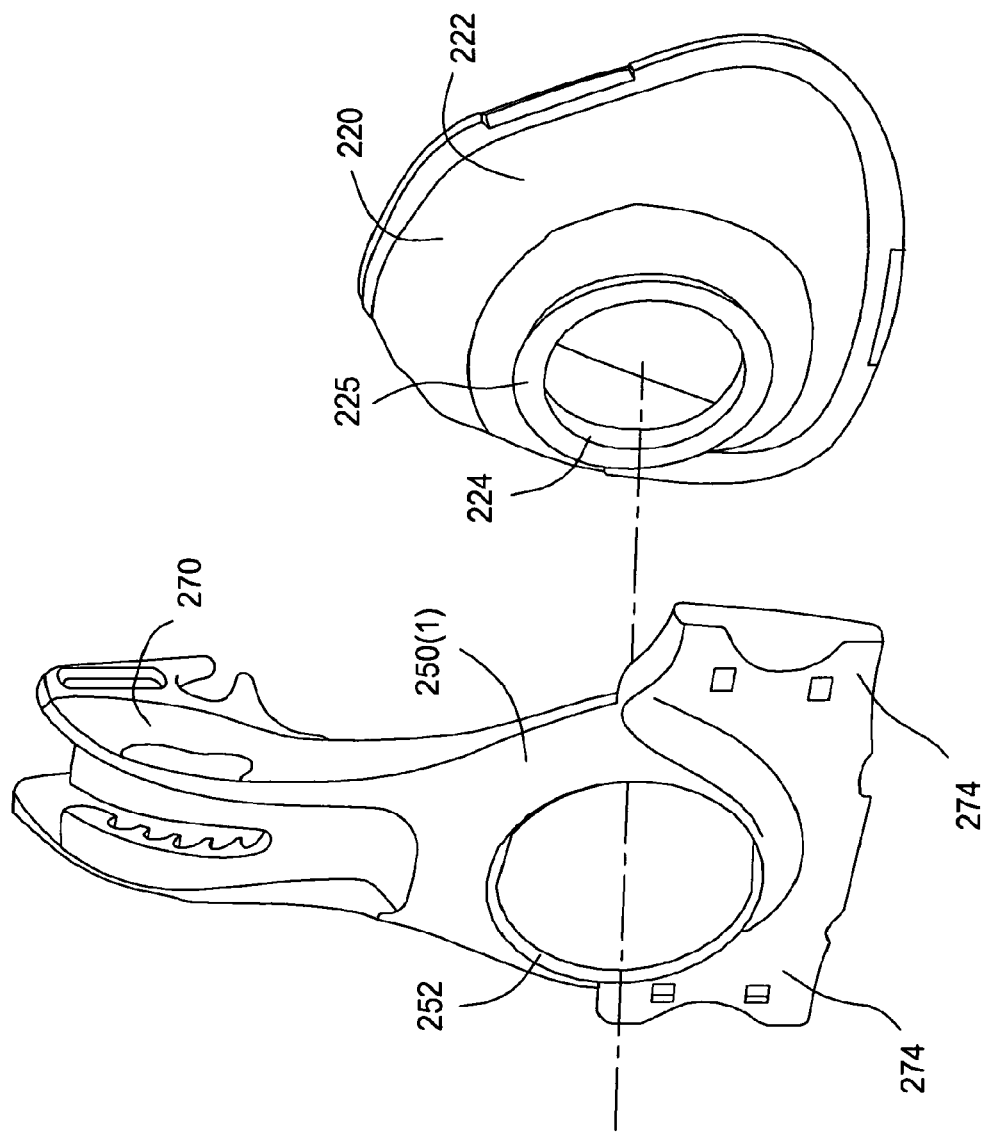
Figure 2B:
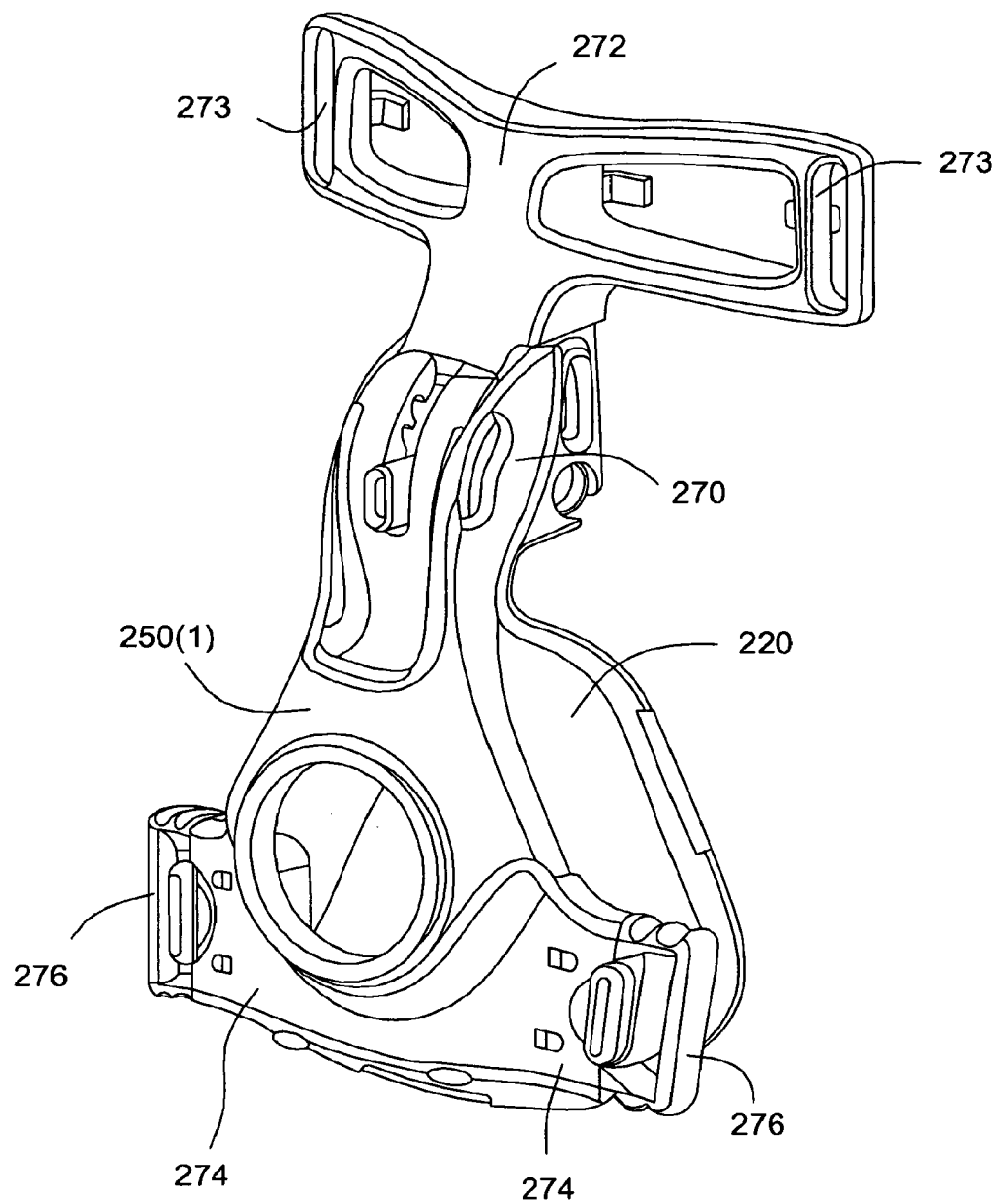

In FIGS. 2A-2B, the headgear connector 250(1) is structured to allow the use of an adjustable forehead support. Specifically, the headgear connector 250(1) includes an upper support member or interface 270 adapted to support a forehead support 272 (e.g., see FIG. 2B), lower headgear clip receptacles 274 adapted to be engaged with respective clips 276 (e.g., see FIG. 2B) provided to lower side straps of the headgear (not shown), and the opening 252 structured to engage the interfacing structure 225 of the frame 220.

In use, the headgear connector 250(1) is attached to the frame 220, the forehead support 272 is adjustably mounted to the upper support member 270 of the headgear connector 250(1) to provide a support and stability mechanism between the mask system and the patient's forehead, and headgear having headgear straps associated with such headgear connector 250(1) and forehead support 272 is attached to the headgear connector 250(1) and forehead support 272 to maintain the mask system in a desired position on the patient's face. As illustrated, the headgear connector 250(1) and forehead support 272 are structured for use with headgear including a pair of lower side straps attached to respective clips 276 and a pair of upper side straps attached to respective openings 273 on the forehead support 272.

2.2 Headgear Connector with Fixed Forehead Support

Figure 3A:
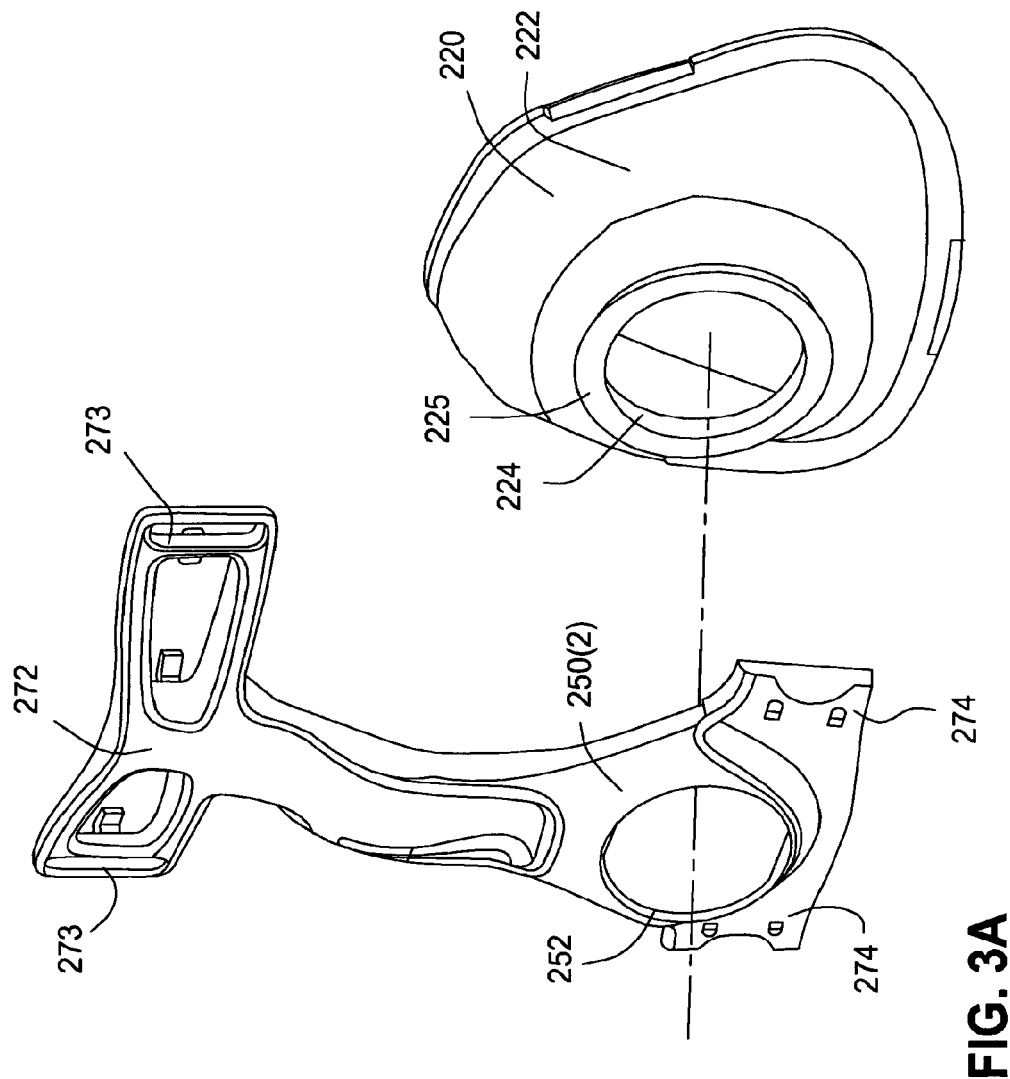
Figure 3B:
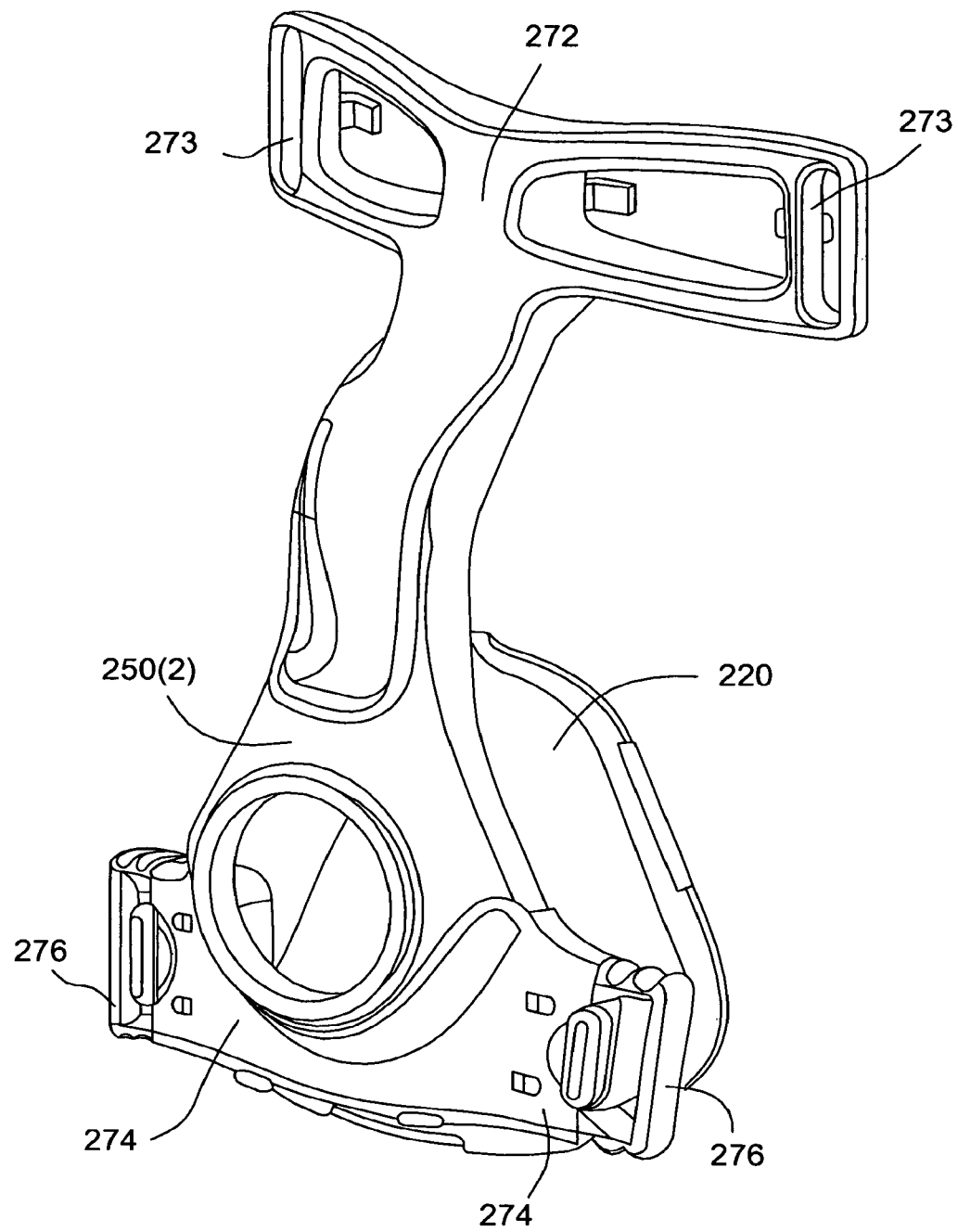

In FIGS. 3A-3B, the headgear connector 250(2) includes a fixed forehead support. Specifically, the headgear connector 250(2) includes a fixed forehead support 272 having openings 273 for attaching respective upper side straps of the headgear, lower headgear clip receptacles 274 adapted to be engaged with respective clips 276 (e.g., see FIG. 3B) provided to lower side straps of the headgear (not shown), and the opening 252 structured to engage the interfacing structure 225 of the frame 220.

In use, the headgear connector 250(2) is attached to the frame 220 and headgear having headgear straps associated with such headgear connector 250(2) is attached to the headgear connector 250(2) to maintain the mask system in a desired position on the patient's face. As illustrated, the headgear connector 250(2) and its fixed forehead support 272 are structured for use with headgear including a pair of lower side straps attached to respective clips 276 and a pair of upper side straps attached to respective openings 273 on the fixed forehead support 272.

2.3 Symmetrical Headgear Connector

Figure 4A:
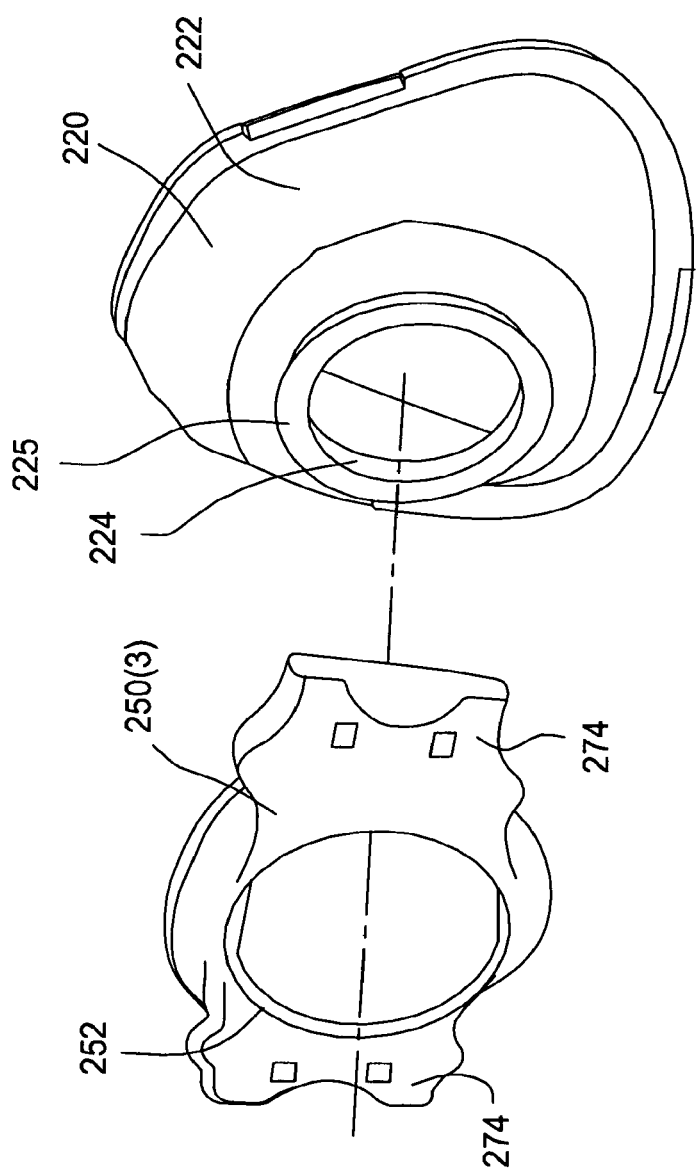
Figure 4B:
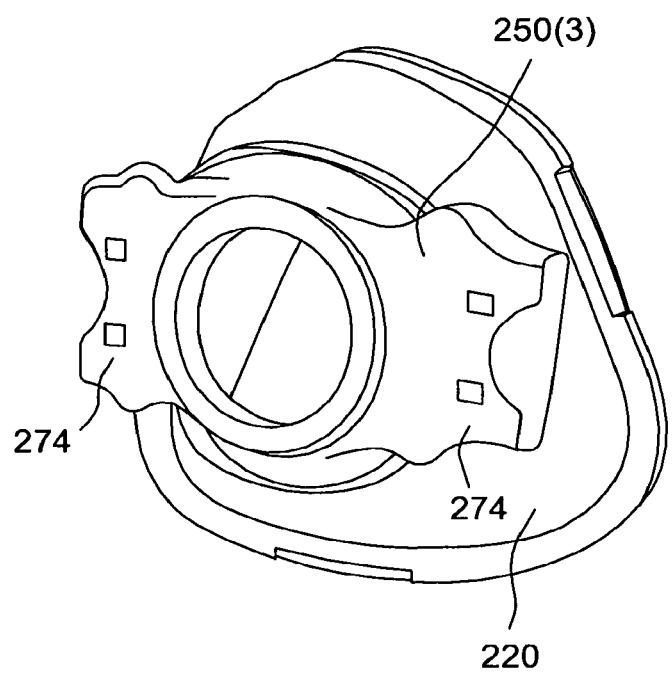

In FIGS. 4A-4B, the headgear connector 250(3) includes a substantially symmetrical arrangement. Specifically, the headgear connector 250(3) includes headgear clip receptacles 274 on each side thereof adapted to be engaged with clips (not shown) provided to side straps of the headgear (not shown) and the opening 252 structured to engage the interfacing structure 225 of the frame 220.

In use, the headgear connector 250(3) is attached to the frame 220 and headgear having headgear straps associated with such headgear connector 250(3) is attached to the headgear connector 250(3) to maintain the mask system in a desired position on the patient's face. As illustrated, the headgear connector 250(3) is structured for use with headgear including a pair of side straps attached to respective clips associated with the clip receptacles 274.

The headgear connector 250(3) is substantially symmetrical about its horizontal and vertical axes such that it may be rotated between two positions with respect to the frame 220, i.e., rotated 180° about its center. In each position, the headgear clip receptacles 274 will be correctly oriented, i.e., extend laterally.

2.4 Headgear Connector with Chin Support/Mouth Seal/Mandibular Device

Figure 5B:
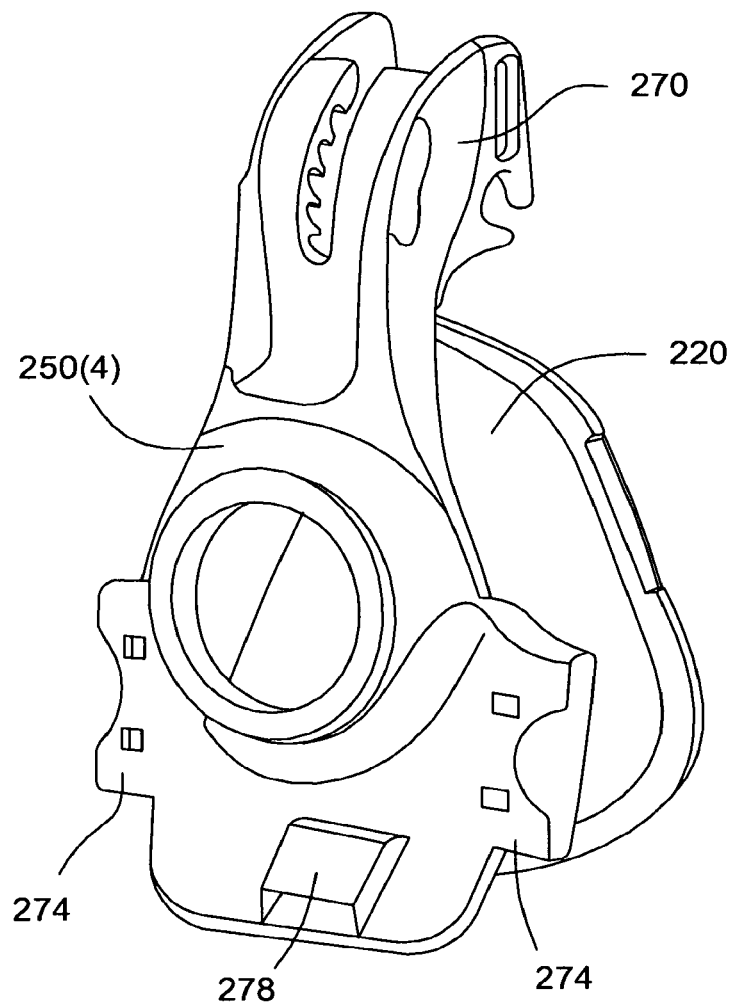

In FIGS. 5A-5B, the headgear connector 250(4) is structured to allow the use of an adjustable forehead support and a chin support, mouth seal, and/or mandibular device, for example. Specifically, the headgear connector 250(4) includes an upper support member or interface 270 adapted to support a forehead support (e.g., such as the forehead support 272 shown in FIG. 2B), lower headgear clip receptacles 274 adapted to be engaged with clips (e.g., such as the clips 276 shown in FIG. 2B) provided to lower side straps of the headgear (not shown), the opening 252 structured to engage the interfacing structure 225 of the frame 220, and a lower clip receptacle 278 positioned at the bottom of the headgear connector 250(4) between the headgear clip receptacles 274 and adapted to be engaged with a clip provided to a chin support, mouth seal, and/or mandibular device, for example.

In use, the headgear connector 250(4) is attached to the frame 220, a forehead support is adjustably mounted to the upper support member 270 of the headgear connector 250(4) to provide a support and stability mechanism between the mask system and the patient's forehead, a chin support, mouth seal, and/or mandibular device, for example, is attached to the headgear connector 250(4) via the lower clip receptacle 278, and headgear having headgear straps associated with such headgear connector 250(4) and forehead support is attached to the headgear connector 250(4) and forehead support to maintain the mask system in a desired position on the patient's face. The headgear connector 250(4) and forehead support are structured for use with headgear including a pair of lower side straps attached to respective clips associated with the clip receptacles 274 and a pair of upper side straps attached to the forehead support.

The lower clip receptacle 278 allows the attachment of devices structured to be positioned at the bottom of the mask system, e.g., below the nose and/or mouth. As noted above, such devices may include a chin support, mouth seal, and/or mandibular device. However, the lower clip receptacle 278 may be structured to support other suitable devices, e.g., chin restraint, chin strap, etc.

2.5 Alternatives

In alternative embodiments, each headgear connector 250(1), 250(2), 250(3), 250(4) may provide openings in place of headgear clip receptacles through which straps of the headgear may pass and be removably connected, e.g., if headgear clips are not desired. Also, the forehead support provided to associated headgear connectors may provide headgear clip receptacles in place of openings for attaching headgear straps.

3. Third Embodiment of Common Frame and Interchangeable Headgear Connector

FIGS. 6A to 6D-2 illustrate a common or universal frame 320 with interchangeable headgear connectors 350(1), 350(2), 350(3) for a mask system according to another embodiment of the present invention. In this embodiment, the mask system includes a nasal interface. Similar to the embodiments described above, this arrangement allows multiple headgear styles to be used with one frame so that different headgear may be mixed and matched with the frame, e.g., depending on patient preference and/or fit.

The common frame 320 includes a main body 322 and a central bore or annular elbow connection seal 324 adapted to engage an elbow assembly. Moreover, the common frame 320 is structured to be selectively and removably coupled to one or more headgear connectors 350(1), 350(2), 350(3) (also referred to as attachment clips). The one or more headgear connectors 350(1), 350(2), 350(3) are selectively arranged on the frame 320 for use with a respective headgear.

Specifically, the frame 320 includes multiple interfacing structures 380(1), 380(2), 380(3) that are adapted to removably connect to a respective one of the headgear connectors 350(1), 350(2), 350(3). The interfacing structures 380(1), 380(2), 380(3) are located in various positions around the frame 320 so that the headgear connectors 350(1), 350(2), 350(3) are attachable to the frame 320 in different positions with respect to one another for use with different headgear arrangements.

In the illustrated embodiment, each interfacing structure 380(1), 380(2), 380(3) provides one or more protrusions having a profile, shape, or arrangement that differs in at least one respect from the other interfacing structures. For example, the first interfacing structure 380(1) at the upper side of the frame provides an elongated, oval-shaped protrusion, the second interfacing structure 380(2) at the lower side of the frame provides an hourglass-shaped or number eight-shaped protrusion, and the third interfacing structure 380(3) at the top of the frame provides spaced apart pegs or pins.

Each headgear connector 350(1), 350(2), 350(3) includes one or more openings having a profile, shape, or arrangement that corresponds to a respective one of the interfacing structures 380(1), 380(2), 380(3). Thus, each headgear connector 350(1), 350(2), 350(3) may attach to the frame in only one orientation to prevent misassembly. That is, the profile, shape, or arrangement of the protrusion/opening provides a keyed arrangement to facilitate assembly of the headgear connector to the frame in the correct position and orientation.

Figure 6A:
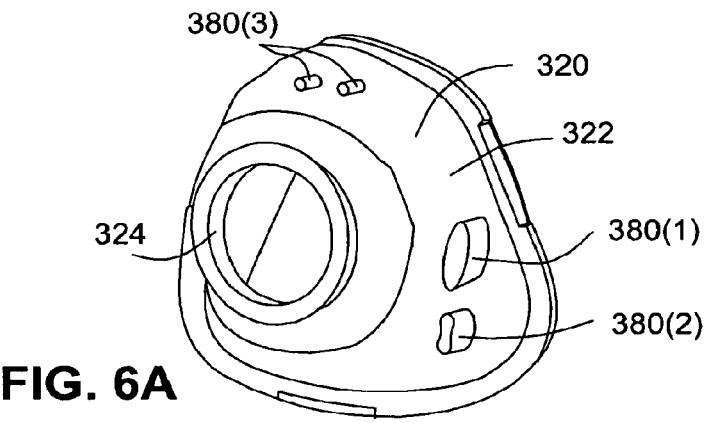
Figures 1, 6B:
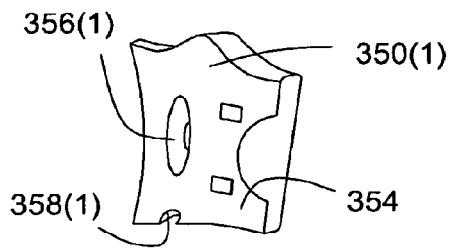

In FIGS. 6B-1 and 6B-2, the headgear connector 350(1) includes a headgear clip receptacle 354 adapted to be engaged with a clip (not shown) provided to a strap of the headgear (not shown), an elongated, oval-shaped opening 356(1) adapted to be engaged with the first interfacing structure 380(1) at the upper side of the frame, and a cutout 358(1) adapted to be engaged with an upper portion of the second interfacing structure 380(2) at the lower side of the frame. The opening 356(1) and cutout 358(1) of the headgear connector 350(1) may engage respective interfacing structures 380(1), 380(2) with a friction fit, snap-fit, and/or mechanical interlock, for example.

Figures 1, 6C:
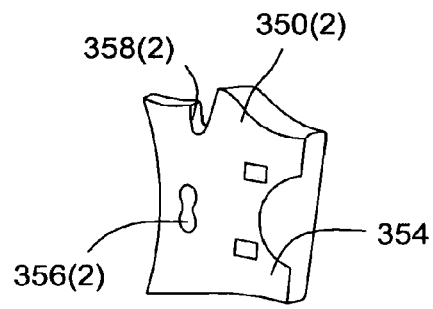
Figures 2, 6B:
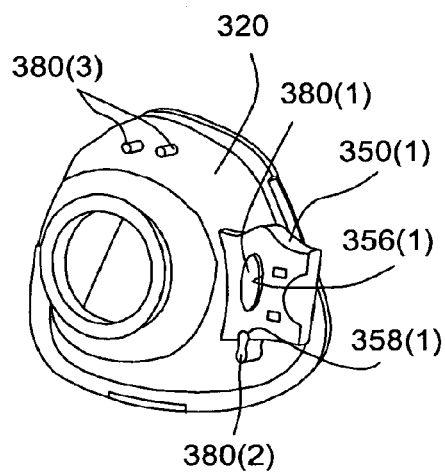
Figures 2, 6C:
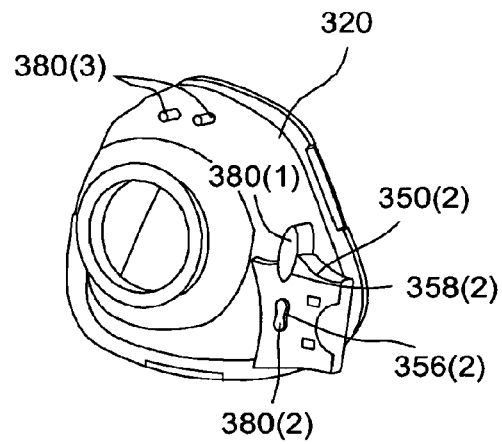

In FIGS. 6C-1 and 6C-2, the headgear connector 350(2) includes a headgear clip receptacle 354 adapted to be engaged with a clip (not shown) provided to a strap of the headgear (not shown), an hourglass-shaped or number eight-shaped opening 356(2) adapted to be engaged with the second interfacing structure 380(2) at the lower side of the frame, and a cutout 358(2) adapted to be engaged with a lower portion of the first interfacing structure 380(1) at the upper side of the frame. The opening 356(2) and cutout 358(2) of the headgear connector 350(2) may engage respective interfacing structures 380(2), 380(1) with a friction fit, snap-fit, and/or mechanical interlock, for example.

Figures 1, 6D:
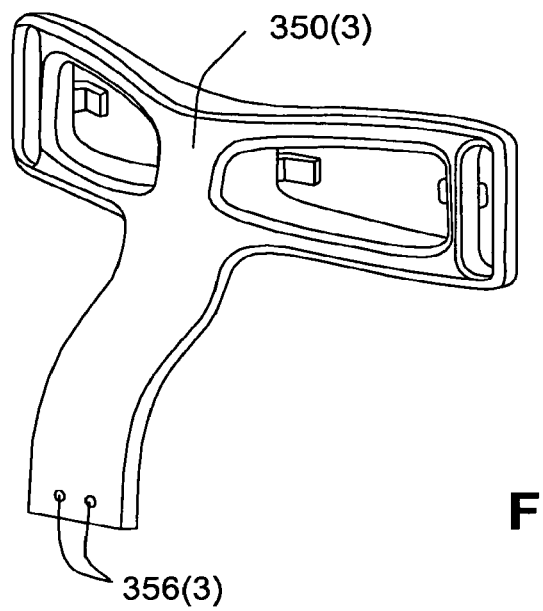
Figures 2, 6D:
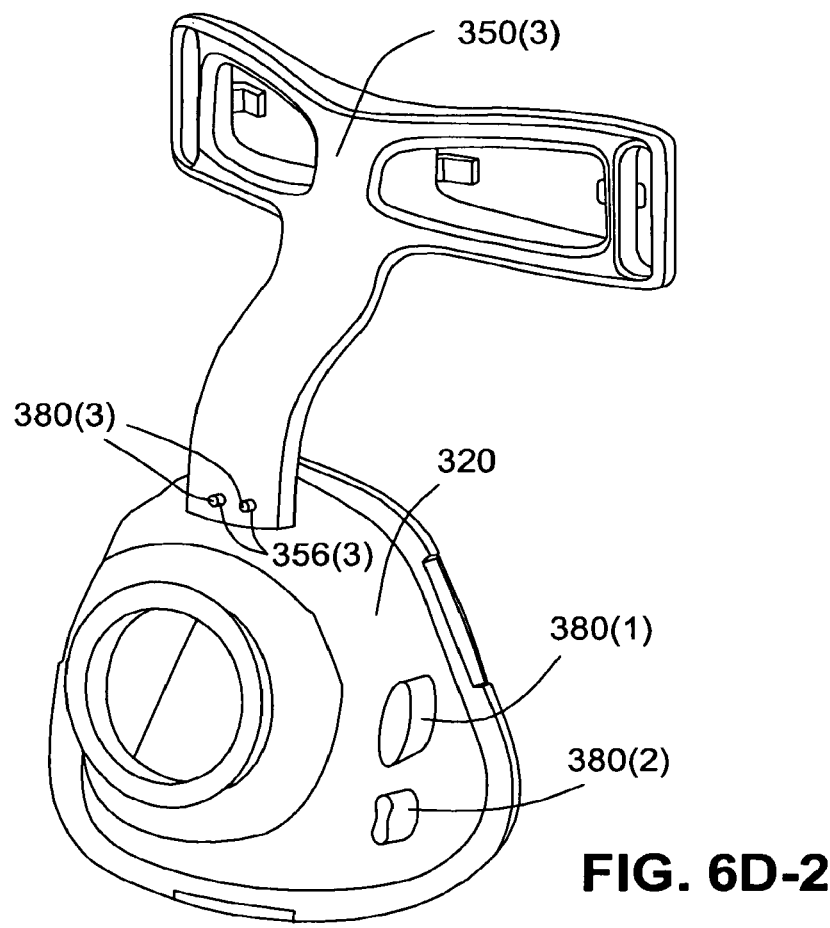

In FIGS. 6D-1 and 6D-2, the headgear connector 350(3) is in the form of a forehead support including spaced apart openings 356(3) adapted to be engaged with respective pegs of the third interfacing structure 380(3) at the top of the frame and openings for attaching respective straps of the headgear. The openings 356(3) of the headgear connector 350(3) may engage respective pegs of the third interfacing structure 380 (3) with a friction fit, snap-fit, and/or mechanical interlock, for example.

It should be appreciated that the headgear connectors may have other suitable styles or arrangements. For example, rather than a forehead support, the headgear connector 350(3) may provide an upper headgear clip receptacle or an upper support member adapted to support a forehead support. Also, in an alternative embodiment, a vertical headgear strap may be structured to directly engage the pegs of the third interfacing structure 380(3).

In use, headgear connectors are selected for use with a particular headgear. That is, each different style of headgear may be associated with headgear connectors having features (i.e., openings having a unique profile, shape, or arrangement) that prevent them from being assembled to the frame in the incorrect position. For example, the headgear connector 350(1) shown in FIGS. 6B-1 and 6B-2 may be associated with headgear having side straps adapted to be positioned at an upper side of the frame 320. The opening 356(1) and cutout 358(1) of the headgear connector 350(1) provide a unique shape that ensures that headgear connector 350(1) is connected to the frame 320 at first interfacing structure 380(1) on an upper side of the frame, rather than at the second interfacing structure 380(2) on a lower side of the frame 320 (i.e., protrusion 380(1) only allows opening 356(1) to pass). The headgear connector 350(3) providing a forehead support may be attached to the top of the frame when headgear having upper side straps is provided, for example.

Thus, the protrusion/opening arrangement (also referred to as poka-yoke design) ensures that only the correct positioning of the headgear connectors for a particular headgear can take place. This arrangement ensures that headgear is correctly assembled to the frame, which leads to correct sealing vectors and improved comfort.

It should be appreciated that the protrusion/opening may have other suitable shapes, and the protrusions may be located in other suitable positions on the frame for attaching headgear connectors or other suitable accessories. In addition, the positioning of the protrusion/opening may be reversed, e.g., opening on frame and protrusion on headgear connector.

4. Fourth Embodiment of Common Frame and Interchangeable Headgear Connector

Figure 7A:
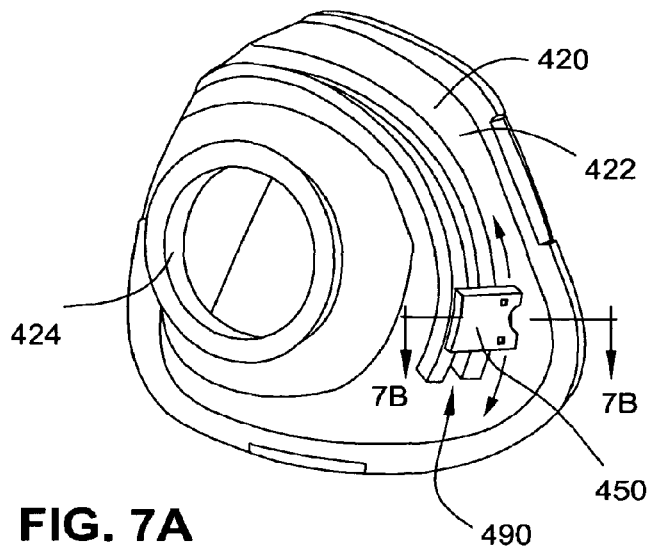
FIGS. 7A to 7C illustrate a common frame with interchangeable and slidable headgear connectors for a mask system according to another embodiment of the present invention.
Figures 1, 7B:
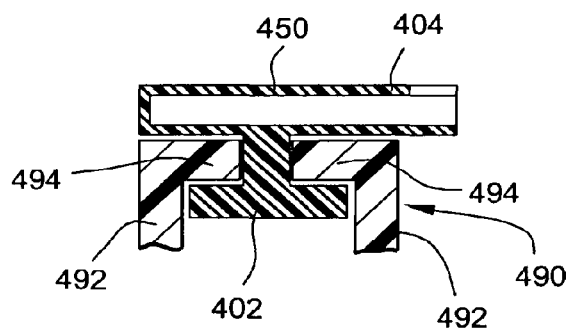
Figures 2, 7B:
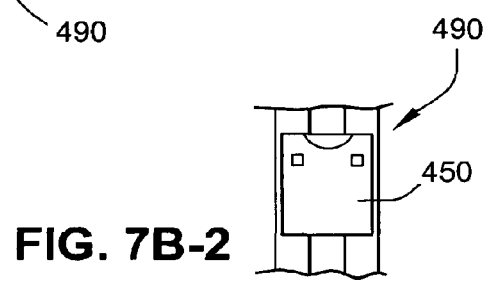
Figures 3, 7B:
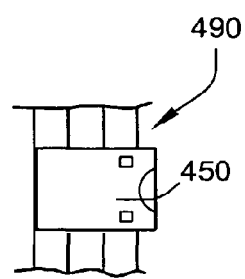
Figure 7C:
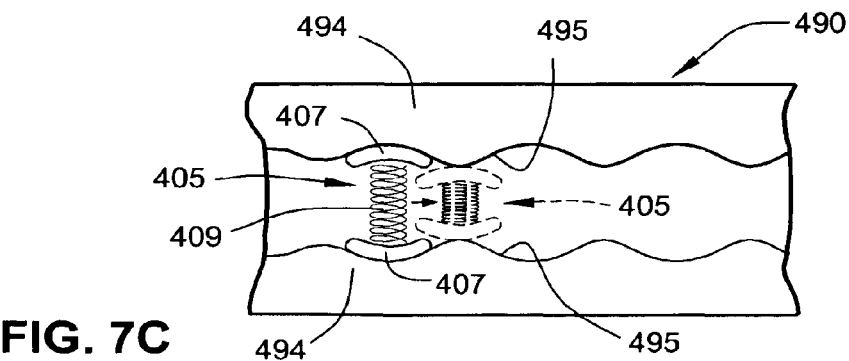

FIGS. 7A to 7C illustrate a common or universal frame 420 with interchangeable and/or slidable headgear connectors 450 for a mask system according to another embodiment of the present invention. In this embodiment, the mask system includes a nasal interface. Similar to the embodiments described above, this arrangement allows multiple headgear styles to be used with one frame so that different headgear may be mixed and matched with the frame, e.g., depending on patient preference and/or fit.

The common frame 420 includes a main body 422 and a central bore or annular elbow connection seal 424 adapted to engage an elbow assembly. Moreover, the common frame 420 is structured to be selectively and removably coupled to one or more headgear connectors 450 (also referred to as attachment clips or sliders). The one or more headgear connectors 450 are selectively arranged on the frame 420 for use with a respective headgear.

Specifically, the frame 420 includes a slider support structure 490 adapted to removably and slidably support one or more headgear connectors 450. Each headgear connectors 450 is slidable along the slider support structure 490 to one of multiple positions. This arrangement allows one or more headgear connectors 450 to be attached to the frame in different positions for use with different headgear arrangements.

In the illustrated embodiment, the slider support structure 490 extends along side and top portions of the frame. However, other suitable arrangements are possible, e.g., slider support structure provided along bottom portion of the frame. As best shown in FIG. 7B-1, the slider support structure 490 includes spaced apart walls 492 each having an inwardly directed flange 494 to prevent the one or more headgear connectors 450 from being pulled outwardly from the frame.

Each headgear connector 450 includes a T-shaped portion 402 adapted to be slidably engaged with the slider support structure 490 (e.g., see FIG. 7B-1) and a clip receptacle 404 adapted to be engaged with a clip (not shown). The clip may be provided to a strap of the headgear or other accessory, e.g., forehead support.

Figures 1, 1D, 2, 3:
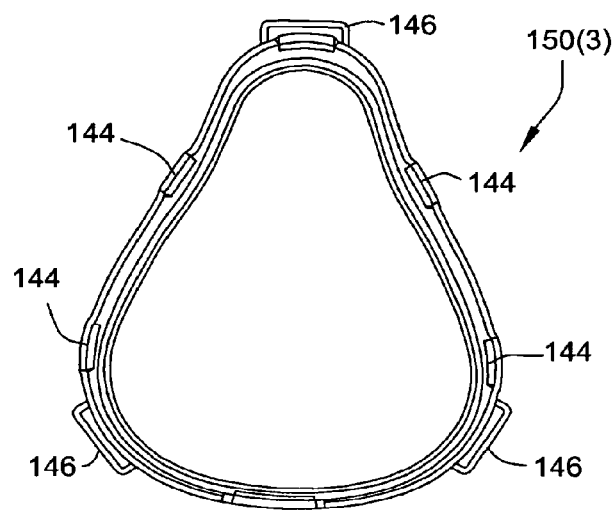
Figures 1, 1D, 2, 3, 4, 5:
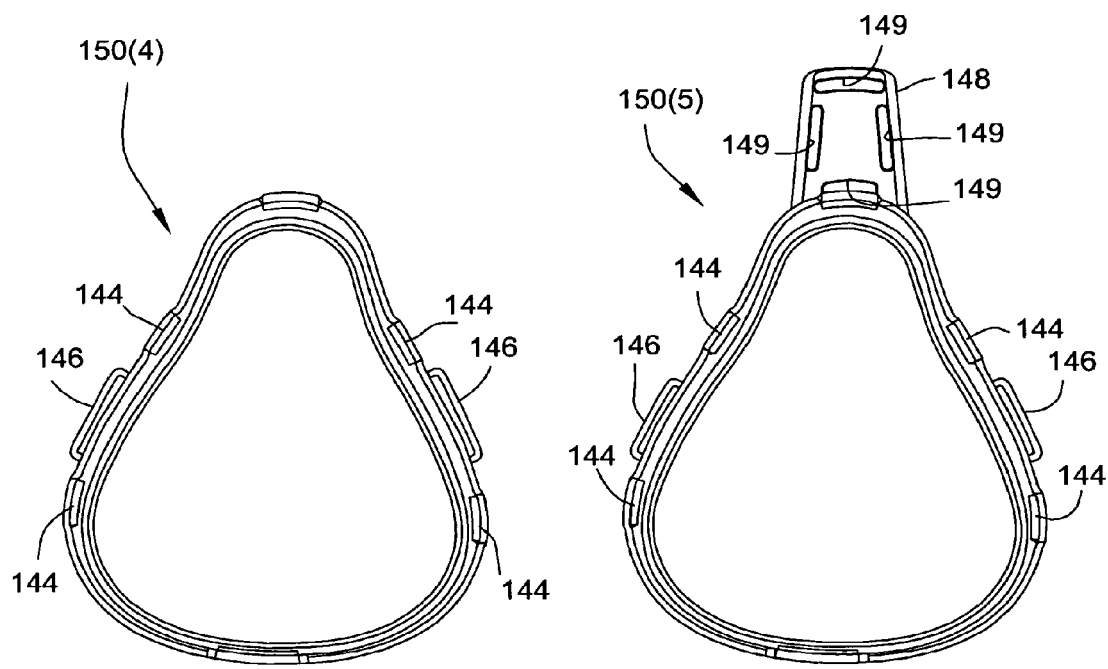

In use, one or more headgear connectors 450 are positioned on the frame 420 for use with a particular headgear. That is, one or more headgear connectors 450 are slid along the slider support structure 490 to a certain position, e.g., depending on the headgear arrangement. The slider support structure and/or headgear connector may include a locking arrangement to lock the headgear connector in position. For example, the headgear connector 450 may be rotatable with respect to the slider support structure 490 between unlocked and locked positions. FIG. 7B-2 shows the headgear connector 450 in an unlocked position that allows the headgear connector 450 to slide freely along the slider support structure 490, and FIG. 7B-3 shows the headgear connector 450 rotated or spun to a locked position that locks the headgear connector 450 in position. In an alternative embodiment, a screw or movable locking member (e.g., push-button release) may be provided to the headgear connector that is adapted to engage the slider support structure to lock the headgear connector in position.

Also, alignment indicators may be provided to the slider support structure and/or headgear connector to indicate the headgear connector's position. In an embodiment, the headgear may be provided with a particular setting of the headgear connectors' positioning.

FIG. 7C illustrates an embodiment of a slider support structure 490 wherein each flange 494 includes a scalloped edge 495. In such an arrangement, each headgear connector may include an interface adapted to be squeezed between the opposing scalloped edges 495. For example, as shown in FIG. 7C, the headgear connector may include a ratcheting mechanism 405 including end portions 407 adapted to engage the edges 495 and a biasing member 409 (e.g., spring) adapted to resiliently bias or force the end portions 407 into engagement with the edges 495. In use, the scalloped edges 495 will hold the ratcheting mechanism 405 in a desired position (as shown in solid lines) and the ratcheting mechanism 495 may be squeezed so that it can compress and move along the slider support structure 490 into another position (as shown in dashed lines). The scalloped edges 495 may provide audible feedback as the headgear connector is slid to a desired position, e.g., clicking.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask for delivering breathable gas to a patient at positive pressure to treat sleep disordered breathing, the mask comprising:
    a mask frame having a central bore, said mask frame having no built-in or integral headgear attachment points;
    a sealing cushion provided to the mask frame and adapted to form a seal with the patient's face; and
    a headgear connector adapted to engage the mask frame, said headgear connector including a pair of lower headgear clip anchors adapted to be engaged with respective ones of a pair of lower headgear clips, said headgear connector including a forehead support connected to the headgear connector by an upper support member, said forehead support including a pair of openings adapted to attach to respective ones of a pair of upper side straps,
    wherein the mask frame is adapted to removably connect to more than one headgear connector, each headgear connector being different in at least one aspect.

2. The mask according to claim 1, wherein the mask frame and the sealing cushion comprise a full-face mask.

3. The mask according to claim 2, wherein the sealing cushion is secured to the mask frame.

4. The mask according to claim 3, wherein at least a portion of said headgear connector is shaped to conform to a portion of said mask frame.

5. The mask according to claim 4, wherein the mask frame includes a peripheral edge to engage the headgear connector.

6. The mask according to claim 1, comprising an elbow assembly, said elbow assembly being adapted to be connected to an air delivery tube.

7. The mask according to claim 1, wherein the headgear connector is removably attachable to the mask frame.

8. The mask according to claim 7, wherein when said mask frame and said headgear connector are attached, the mask frame and the headgear connector are not movable relative to one another.

9. The mask according to claim 7, wherein the headgear connector and the mask frame are adapted to be engaged by a snap-fit.

10. The mask according to claim 7, wherein the headgear connector comprises a plurality of tabs to attach the mask frame with a snap-fit.

11. The mask according to claim 1, wherein the central bore is located on a main body of the mask frame.

12. The mask according to claim 1, comprising a vent assembly for gas washout.

13. The mask according to claim 1, wherein the forehead support is T-shaped.

14. The mask according to claim 1, wherein the sealing cushion cannot be easily detached from the mask frame.

15. The mask according to claim 14, wherein the sealing cushion and the mask frame are permanently attached.

16. The mask according to claim 1, wherein said headgear connector is constructed of a similar material as the frame.

17. The mask according to claim 16, wherein said headgear connector and said mask frame are constructed of a substantially rigid, non-malleable plastic material.

18. The mask according to claim 17, wherein said headgear connector and said mask frame are constructed of polycarbonate.

19. A mask system for delivering breathable gas to a patient at positive pressure to treat sleep disordered breathing, the mask system comprising:
    a headgear including a pair of upper side straps, a pair of lower side straps, and a rear portion;
    a pair of lower headgear clips adapted to receive respective ones of the pair of lower side straps; and
    a mask according to claim 1.

20. The mask system according to claim 19, wherein the pair of upper side straps are arranged to extend above the patient's ears and the pair of lower side straps are arranged to extend below the patient's ears.

21. The mask system according to claim 20, wherein the rear portion of the headgear is adapted to cup the occiput of the patient's head.

22. The mask according to claim 1, wherein said forehead support is adjustable.

23. A mask for delivering breathable gas to a patient at positive pressure to treat sleep disordered breathing, the mask comprising:
- a rigid mask frame having a bore and an interfacing structure associated with the bore, said mask frame having no built-in or integral headgear attachment points;
- a sealing cushion provided to the mask frame and adapted to form a seal with the patient's face, the mask frame and the sealing cushion together forming a breathing cavity; and
- a headgear connector adapted to engage the interfacing structure with a snap-fit, said headgear connector including a pair of lower headgear clip anchors adapted to be engaged with respective ones of a pair of lower headgear clips to attach a pair of lower side straps, said headgear connector including a fixed forehead support, said fixed forehead support including a pair of openings adapted to attach to respective ones of a pair of upper side straps.

24. The mask according to claim 23, wherein the mask frame and the sealing cushion comprise a full-face mask.

25. The mask according to claim 24, wherein the sealing cushion is secured to the mask frame.

26. The mask according to claim 25, wherein at least a portion of said headgear connector is shaped to conform to a portion of said mask frame.

27. The mask according to claim 23, further comprising an elbow assembly, said elbow assembly being adapted to be connected to an air delivery tube to deliver the breathable gas to the breathing cavity.

28. The mask according to claim 23, wherein the headgear connector is removably attachable to the mask frame.

29. The mask according to claim 28, wherein when said mask frame and said headgear connector are attached, the mask frame and the headgear connector are not movable relative to one another.

30. The mask according to claim 23, wherein the bore is located on a front face of the mask frame.

31. The mask according to claim 23, comprising a vent assembly for gas washout.

32. The mask according to claim 23, wherein the fixed forehead support is T-shaped.

33. The mask according to claim 23, wherein the sealing cushion and the mask frame are permanently attached.

34. The mask according to claim 23, wherein said headgear connector is constructed of a similar material as the mask frame.

35. The mask according to claim 23, wherein said headgear connector and said mask frame are constructed of a substantially rigid, non-malleable plastic material.

36. The mask according to claim 35, wherein said headgear connector and said mask frame are constructed of polycarbonate.

37. The mask according to claim 23, further comprising:
- an elbow assembly, said elbow assembly being adapted to be connected to an air delivery tube to deliver the breathable gas to the breathing cavity; and
- a vent assembly for gas washout,
- wherein the mask frame and the sealing cushion comprise a full-face mask,
- wherein at least a portion of said headgear connector is shaped to conform to a portion of said mask frame,
- wherein the headgear connector is removably attachable to the mask frame,
- wherein when said mask frame and said headgear connector are attached, the mask frame and the headgear connector are not movable relative to one another,
- wherein the sealing cushion and the mask frame are permanently attached, and
- wherein said headgear connector and said mask frame are constructed of a substantially rigid, non-malleable plastic material.

38. A mask system for delivering breathable gas to a patient at positive pressure to treat sleep disordered breathing, the mask system comprising:
- a headgear including the pair of upper side straps, the pair of lower side straps, and a rear portion; and
- the mask according to claim 23,
- wherein the pair of lower headgear clips are adapted to receive respective ones of the pair of lower side straps.

39. The mask system according to claim 38, wherein the pair of upper side straps are arranged to extend above the patient's ears and the pair of lower side straps are arranged to extend below the patient's ears.

40. The mask system according to claim 39, wherein the rear portion of the headgear is adapted to cup the occiput of the patient's head.

41. A mask for delivering breathable gas to a patient at positive pressure to treat sleep disordered breathing, the mask comprising:
- a one-piece rigid mask frame having a bore and an interfacing structure at least partly surrounding the bore, the rigid mask frame having no built-in or integral headgear attachment points;
- a soft sealing cushion provided to the rigid mask frame and adapted to form a seal with the patient's face;
- an elbow assembly, said elbow assembly being adapted to be connected to an air delivery tube to deliver the breathable gas to a breathing cavity defined by the rigid mask frame and the soft sealing cushion; and
- a headgear connector having an opening and an attachment structure associated with the opening, the attachment structure being adapted to engage the interfacing structure of the rigid mask frame to removably connect the headgear connector to the rigid mask frame, said bore and said opening being concentrically disposed about a common axis,
- wherein the headgear connector and the rigid mask frame are detachably connected together by translating the rigid mask frame and the headgear connector towards one another along the common axis until a snap-fit connection is established between the attachment structure of the headgear connector and the interfacing structure of the rigid mask frame, and
- wherein said headgear connector includes a fixed forehead support.

42. The mask according to claim 41, wherein the rigid mask frame and the soft sealing cushion comprise a full-face mask.

43. The mask according to claim 41, wherein the soft sealing cushion is secured to the rigid mask frame.

44. The mask according to claim 41, wherein at least a portion of said headgear connector is shaped to conform to a portion of said rigid mask frame.

45. The mask according to claim 41, wherein when said rigid mask frame and said headgear connector are attached, the rigid mask frame and the headgear connector are not movable relative to one another.

46. The mask according to claim 41, wherein the bore is located on a front face of the rigid mask frame.

47. The mask according to claim 41, comprising a vent assembly for gas washout.

48. The mask according to claim 41, wherein the fixed forehead support is T-shaped.

49. The mask according to claim 41, wherein the soft sealing cushion and the rigid mask frame are permanently attached.

50. The mask according to claim 41, wherein said headgear connector is constructed of a similar material as the rigid mask frame.

51. The mask according to claim 41, wherein said headgear connector and said rigid mask frame are constructed of a substantially rigid, non-malleable plastic material.

52. The mask according to claim 51, wherein said headgear connector and said rigid mask frame are constructed of polycarbonate.

53. The mask according to claim 41, further comprising a vent assembly for gas washout,
wherein the rigid mask frame and the soft sealing cushion comprise a full-face mask,
wherein at least a portion of said headgear connector is shaped to conform to a portion of said rigid mask frame,
wherein when said rigid mask frame and said headgear connector are attached, the rigid mask frame and the headgear connector are not movable relative to one another,
wherein the soft sealing cushion and the rigid mask frame are permanently attached, and
wherein said headgear connector and said rigid mask frame are constructed of a substantially rigid, non-malleable plastic material.

54. A mask system for delivering breathable gas to a patient at positive pressure to treat sleep disordered breathing, the mask system comprising:
a headgear including a pair of upper side straps, a pair of lower side straps, and a rear portion;
a pair of lower headgear clip anchors formed on said headgear connector and adapted to be engaged with respective ones of a pair of lower headgear clips to attach the pair of lower side straps, the pair of lower headgear clips being adapted to receive respective ones of the pair of lower side straps;
a pair of openings formed on said forehead support adapted to attach to respective ones of the pair of upper side straps; and
the mask according to claim 41.

55. The mask system according to claim 54, wherein the pair of upper side straps are arranged to extend above the patient's ears and the pair of lower side straps are arranged to extend below the patient's ears.

56. The mask system according to claim 55, wherein the rear portion of the headgear is adapted to cup the occiput of the patient's head.

57. A mask system for delivering breathable gas to a patient at positive pressure to treat sleep disordered breathing, the mask system comprising:
a rigid mask frame having a bore and a cylindrical projection extending around the bore, the rigid mask frame having no built-in or integral headgear attachment points;
a soft sealing cushion provided to the rigid mask frame and adapted to form a seal with the patient's face, said soft sealing cushion and said rigid mask frame defining a breathing cavity from which the breathable gas is accessible by the patient in use;
an elbow having a first end adapted to be connected to an air delivery tube and a second end in communication with the bore to deliver the breathable gas from the air delivery tube to the breathing cavity;
headgear including a pair of upper side straps, a pair of lower side straps, and a rear portion from which the upper side straps and the lower side straps extend; and
a headgear connector having an opening with an attachment structure associated with the opening, the attachment structure removably attached to the cylindrical projection of the rigid mask frame with a snap-fit such that when said cylindrical projection and said attachment structure are attached, the rigid mask frame and the headgear connector are not movable relative to one another,
wherein said opening and said bore are concentrically disposed about a common axis,
wherein said headgear connector includes a pair of lower headgear clip anchors adapted to secure respective ones of the lower side straps, and
wherein said headgear connector includes a forehead support including a pair of openings adapted to attach to respective ones of the pair of upper side straps.

58. The mask system according to claim 57, wherein the rigid mask frame and the soft sealing cushion comprise a full-face mask.

59. The mask system according to claim 57, wherein the soft sealing cushion is secured to the rigid mask frame.

60. The mask system according to claim 57, wherein an inner surface of said headgear connector is shaped to conform to an outer surface of said rigid mask frame.

61. The mask system according to claim 57, wherein the forehead support is adapted to contact the patient's forehead in use.

62. The mask system according to claim 57, wherein the bore is located on a main body of the rigid mask frame.

63. The mask system according to claim 57, comprising a vent assembly for gas washout.

64. The mask system according to claim 57, wherein the forehead support is T-shaped.

65. The mask system according to claim 57, wherein the soft sealing cushion and the rigid mask frame are permanently attached.

66. The mask system according to claim 57, wherein said headgear connector is constructed of a similar material as the rigid frame.

67. The mask system according to claim 57, wherein said headgear connector and said mask frame are constructed of a substantially rigid, non-malleable plastic material.

68. The mask system according to claim 67, wherein said headgear connector and said rigid mask frame are constructed of polycarbonate.

69. The mask system according to claim 57, wherein the attachment structure and the cylindrical projection are engaged with the snap-fit when the attachment structure and the cylindrical projection are engaged in a nested arrangement.

70. The mask system according to claim 57, further comprising a vent assembly for gas washout,
wherein the rigid mask frame and the soft sealing cushion comprise a full-face mask,
wherein an inner surface of said headgear connector is shaped to conform to an outer surface of said mask frame,
wherein the forehead support is adapted to contact the patient's forehead in use,
wherein the soft sealing cushion and the rigid mask frame are permanently attached, and
wherein said headgear connector and said rigid mask frame are constructed of a substantially rigid, non-malleable plastic material.

71. The mask system according to claim 57, wherein the pair of upper side straps are arranged to extend above the patient's ears and the pair of lower side straps are arranged to extend below the patient's ears.

72. The mask system according to claim 71, wherein the rear portion of the headgear is adapted to cup the occiput of the patient's head.

73. A mask for delivering breathable gas to a patient at positive pressure to treat sleep disordered breathing, the mask comprising:
   a rigid mask frame having a bore and no built-in or integral headgear attachment points;
   a soft sealing cushion attached to the rigid mask frame and adapted to form a seal with the patient's face, the rigid mask frame and the soft sealing cushion together forming a breathing cavity to receive the breathable gas; and
   a headgear connector including a plurality of tabs structured to removably attach the headgear connector to the rigid mask frame with a snap-fit, a pair of crossbars to removably attach a pair of lower side straps, and an extension having a plurality of openings to removably attach a pair of upper side straps.

74. The mask according to claim 73, wherein the rigid mask frame and the soft sealing cushion comprise a full-face mask.

75. The mask according to claim 74, wherein the soft sealing cushion is secured to the mask frame.

76. The mask according to claim 73, further comprising an elbow adapted to be connected to an air delivery tube to deliver the breathable gas to the breathing cavity.

77. The mask according to claim 73, wherein when said rigid mask frame and said headgear connector are attached, the rigid mask frame and the headgear connector are not movable relative to one another.

78. The mask according to claim 73, wherein the bore is located on a front face of the rigid mask frame.

79. The mask according to claim 73, wherein the rigid mask frame further comprises a vent assembly for gas washout.

80. The mask according to claim 73, wherein said headgear connector is constructed of a similar material as the rigid mask frame.

81. The mask according to claim 73, wherein said headgear connector and said rigid mask frame are constructed of a substantially rigid, non-malleable plastic material.

82. The mask according to claim 81, wherein said headgear connector and said rigid mask frame are constructed of polycarbonate.

83. The mask according to claim 73, further comprising:
   an elbow adapted to be connected to an air delivery tube to deliver the breathable gas to the breathing cavity,
   wherein the rigid mask frame further comprises a vent assembly for gas washout,
   wherein the rigid mask frame and the soft sealing cushion comprise a full-face mask,
   wherein when said rigid mask frame and said headgear connector are attached, the rigid mask frame and the headgear connector are not movable relative to one another, and
   wherein said headgear connector and said rigid mask frame are constructed of a substantially rigid, non-malleable plastic material.

84. A mask system for delivering breathable gas to a patient at positive pressure to treat sleep disordered breathing, the mask system comprising:
   a headgear including the pair of upper side straps, the pair of lower side straps, and a rear portion; and
   a mask according to claim 73.

85. The mask system according to claim 84, wherein the pair of upper side straps are arranged to extend above the patient's ears and the pair of lower side straps are arranged to extend below the patient's ears.

86. The mask system according to claim 85, wherein the rear portion of the headgear is adapted to cup the occiput of the patient's head.

* * * * *